United States Patent
Landry et al.

(10) Patent No.: US 6,557,226 B1
(45) Date of Patent: May 6, 2003

(54) APPARATUS FOR MANUFACTURING A BONE DOWEL

(76) Inventors: Michael E. Landry, 4808 Senora Creek Ct., Austin, TX (US) 78735; Erik J. Wagner, 16920 Squaw Valley La., Austin, TX (US) 78717

( * ) Notice: Subject to any disclaimer, the term of this patent is extended or adjusted under 35 U.S.C. 154(b) by 0 days.

(21) Appl. No.: 09/369,964

(22) Filed: Aug. 6, 1999

Related U.S. Application Data

(63) Continuation-in-part of application No. 09/298,269, filed on Apr. 23, 1999.

(51) Int. Cl.$^7$ ............................. B23B 3/26; B23C 3/32
(52) U.S. Cl. ................... 29/27 C; 29/27 A; 29/560; 82/110; 82/152; 408/23; 409/66; 409/165
(58) Field of Search ........................ 29/27 R, 27 A, 29/27 C, 560; 409/165, 134, 214, 218, 138, 66; 408/103, 23, 26; 82/110, 162, 152

(56) References Cited

U.S. PATENT DOCUMENTS

| | | | |
|---|---|---|---|
| 1,358,040 | A | 11/1920 | Trundle, Jr. |
| 2,028,727 | A | 1/1936 | Perry et al. |
| 2,370,286 | A | 2/1945 | Berger |
| 2,378,302 | A | 6/1945 | Kline |

(List continued on next page.)

FOREIGN PATENT DOCUMENTS

| | | |
|---|---|---|
| DE | 43 23 956 | 10/1994 |
| EP | 0 260 044 | 3/1988 |
| EP | 307 241 | 3/1989 |
| ES | 9500308 | 2/1995 |
| FR | 2 717 068 | 9/1995 |
| GB | 2025282 | 1/1980 |
| JP | 86407 | 4/1991 |
| SU | 1424826 | 9/1988 |
| WO | 88/06943 | 9/1988 |
| WO | 97/00054 | 1/1997 |
| WO | 97/06753 | 2/1997 |
| WO | 98/17209 | 4/1998 |
| WO | 98/55052 | 12/1998 |

OTHER PUBLICATIONS

Albee et al., *Bone Graft Surgery in Disease, Injury and Deformity*, D. Appleton–Century Co., Inc., 1940, pp. xi–xv, 1–31, 48–107, and 210–227.

Vich, "Update of the Cloward procedure: new instruments," J. Neurosurg., vol. 81, Nov. 1994, pp. 716–720.

Vich, "Anterior cervical interbody fusiion with threaded cylindrical bone," J. Neurosurg., vol. 63, Nov. 1985, pp. 750–753.

"Introducing the EndoDowel™," Musculoskeletal Transplant Foundation, Oct. 1996.

Catalog from Musculoskeletal Transplant Foundation, Apr. 1996.

(List continued on next page.)

*Primary Examiner*—William Briggs

(57) ABSTRACT

Apparatus for manufacturing a bone dowel includes a machine base with tracks on a surface thereof. Modules configured to slide in the tracks may include a module for a high speed rotary tool, a collet module, a vise module and a threading module. A vise module may include a base configured to slide in the tracks of the machine base, a frame configured to slide on the vise module base, two opposing vise jaws held within the frame, a spring device between the vise jaws, and a press that sits on top of the vise jaws within the frame. A bone dowel manufactured using the apparatus may include smoothed ends, a slot on one end, a canal running through the dowel perpendicular to the long axis, a hole running through the dowel along the long axis, and threads on the outer surface.

79 Claims, 21 Drawing Sheets

U.S. PATENT DOCUMENTS

| | | |
|---|---|---|
| 2,388,152 A | 10/1945 | Jarvis et al. |
| 3,222,052 A | 12/1965 | Freda |
| 3,470,789 A | 10/1969 | Morse |
| 3,704,648 A | 12/1972 | Burfoot |
| 3,848,601 A | 11/1974 | Ma et al. |
| 3,988,814 A * | 11/1976 | Hoffman .................... 29/27 C |
| 4,044,650 A * | 8/1977 | Lyon et al. ............. 409/165 X |
| 4,057,893 A * | 11/1977 | Smith et al. .................. 24/560 |
| 4,401,112 A | 8/1983 | Rezaian |
| 4,501,269 A | 2/1985 | Bagby |
| 4,515,191 A * | 5/1985 | Fetty ........................ 29/500 X |
| 4,566,169 A | 1/1986 | Vesely |
| 4,625,377 A | 12/1986 | Kavthekar |
| 4,714,469 A | 12/1987 | Kenna |
| 4,719,676 A | 1/1988 | Sansone |
| 4,743,146 A | 5/1988 | Khmelnitsky et al. |
| 4,743,256 A | 5/1988 | Brantigan |
| 4,777,713 A | 10/1988 | Kitamura |
| 4,834,757 A | 5/1989 | Brantigan |
| 4,856,503 A | 8/1989 | Schelhas |
| 4,863,476 A | 9/1989 | Sheppard |
| 4,867,620 A * | 9/1989 | Newman et al. ............ 409/134 |
| 4,877,020 A | 10/1989 | Vich |
| 4,878,915 A | 11/1989 | Brantigan |
| 4,904,261 A | 2/1990 | Dove et al. |
| 4,936,848 A | 6/1990 | Bagby |
| 4,950,296 A | 8/1990 | McIntyre |
| 4,961,740 A | 10/1990 | Ray et al. |
| 5,015,247 A | 5/1991 | Michelson |
| 5,015,255 A | 5/1991 | Kuslich |
| 5,026,373 A | 6/1991 | Ray et al. |
| 5,052,089 A * | 10/1991 | Gadaud et al. ............. 29/27 R |
| 5,055,104 A | 10/1991 | Ray |
| 5,090,279 A * | 2/1992 | Enzinger .................... 29/27 A |
| 5,112,354 A | 5/1992 | Sires |
| 5,123,926 A | 6/1992 | Pisharodi |
| 5,147,402 A | 9/1992 | Bohler et al. |
| 5,171,278 A | 12/1992 | Pisharodi |
| 5,192,327 A | 3/1993 | Brantigan |
| 5,263,953 A | 11/1993 | Bagby |
| 5,301,405 A * | 4/1994 | Maker ........................ 29/26 A |
| 5,306,307 A | 4/1994 | Senter et al. |
| 5,306,309 A | 4/1994 | Wagner et al. |
| 5,333,657 A * | 8/1994 | Hart ...................... 409/165 X |
| 5,336,240 A | 8/1994 | Metzler et al. |
| 5,370,697 A | 12/1994 | Baumgartner |
| 5,390,683 A | 2/1995 | Pisharodi |
| 5,397,364 A | 3/1995 | Kozak et al. |
| 5,425,772 A | 6/1995 | Brantigan |
| 5,443,514 A | 8/1995 | Steffee |
| 5,458,638 A | 10/1995 | Kuslich et al. |
| 5,484,437 A | 1/1996 | Michelson |
| 5,489,307 A | 2/1996 | Kuslich et al. |
| 5,489,308 A | 2/1996 | Kuslich et al. |
| 5,505,732 A | 4/1996 | Michelson |
| 5,522,899 A | 6/1996 | Michelson |
| 5,536,271 A | 7/1996 | Daly et al. |
| 5,571,192 A | 11/1996 | Schönhöffer |
| 5,593,409 A | 1/1997 | Michelson |
| 5,601,556 A | 2/1997 | Pisharodi |
| 5,607,424 A | 3/1997 | Tropiano |
| 5,609,635 A | 3/1997 | Michelson |
| 5,609,636 A | 3/1997 | Kohrs et al. |
| 5,632,747 A | 5/1997 | Scarborough et al. |
| 5,645,598 A | 7/1997 | Brosnahan, III |
| 5,653,763 A | 8/1997 | Errico et al. |
| 5,658,337 A | 8/1997 | Kohrs et al. |
| 5,665,122 A | 9/1997 | Kambin |
| 5,669,909 A | 9/1997 | Zdeblick et al. |
| 5,674,295 A | 10/1997 | Ray et al. |
| 5,674,296 A | 10/1997 | Bryan et al. |
| 5,676,701 A | 10/1997 | Yuan et al. |
| 5,683,394 A | 11/1997 | Rinner |
| 5,688,279 A | 11/1997 | McNulty et al. |
| 5,693,100 A | 12/1997 | Pisharodi |
| 5,697,977 A | 12/1997 | Pisharodi |
| 5,700,291 A | 12/1997 | Kuslich et al. |
| 5,702,391 A | 12/1997 | Lin |
| 5,702,449 A | 12/1997 | McKay |
| 5,702,450 A | 12/1997 | Bisserie |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,709,683 A | 1/1998 | Bagby |
| 5,713,899 A | 2/1998 | Marnay et al. |
| 5,716,359 A | 2/1998 | Ojima et al. |
| 5,716,415 A | 2/1998 | Steffee |
| 5,716,416 A | 2/1998 | Lin |
| 5,720,746 A | 2/1998 | Soubeiran |
| 5,720,748 A | 2/1998 | Kuslich et al. |
| 5,722,977 A | 3/1998 | Wilhelmy |
| 5,749,916 A | 5/1998 | Richelsoph |
| 5,766,253 A | 6/1998 | Brosnahan, III |
| 5,776,199 A | 7/1998 | Michelson |
| 5,782,919 A | 7/1998 | Zdeblick et al. |
| 5,785,710 A | 7/1998 | Michelson |
| 5,797,917 A | 8/1998 | Boyd et al. |
| 5,814,084 A | 9/1998 | Grivas et al. |
| 5,964,016 A | 10/1999 | Ito et al. |
| 6,096,081 A | 8/2000 | Grivas et al. |
| 6,095,728 A * | 9/2000 | Howie ........................ 409/214 |
| 6,131,259 A * | 10/2000 | Stark et al. ................. 29/27 R |
| 6,155,756 A * | 12/2000 | Merkle et al. ................ 409/66 |
| 6,231,577 B1 * | 5/2001 | Canedy ..................... 409/138 |

OTHER PUBLICATIONS

"The MTF EndoDowel™," Musculoskeletal Transplant Foundatin, 1996.

"Laparoscopic Bone Dowel Instruments," Sofamor Danek, 1995.

"Laparoscopic Bone Dowel Surgical Technique," Sofamor Danek, 1995.

Brantigan et al, "A Carbon Fiber Implant to Aid Interbody Lumbar Fusion Mechanical Testing," Spine, vol. 16, No. 6 Supplement, 1991.

"Trends in Spine & Disc Surger," MedPro Month, Nov. 1996.

Wittenberg et al., "Compressive Strength of Autologous and Allogenous Bone Grafts for Thoracolumbar and Cervical Spine Fusion," Spine, vol. 15, No. 10, 1990, pp. 1073–1078.

"Spinal Fusion Surgery and the BAK™ Interbody Fusion System," Spine Tech, Inc., 1993.

"BAK®/Cervical Interbody Fusion System," Spine Tech, Inc., 1994.

"The BAK™ Interbody Fusion System," Spine Tech, Inc., 1996.

"BAK™ Interbody Fusion System (Porosity)," Spine Tech, Inc., 1996.

"BAK™ Interbody Fusion System (Biomechanics)," Spine Tech, Inc., 1996.

"BAK™ Interbody Fusion System (Instrumentation)," Spine Tech, Inc., 1996.

"Bone Harvester," Spine Tech, Inc., 1996.

"Biomechanical Rationale, The BAK™ Interbody Fusion System: An Innovative Solution," Spine Tech, Inc., 1994.

"Surgical Technique using Bone Dowel Instrumentation, for Anterior Approach," Sofamor Danek, 1996.

"Surgical Technique using Bone Dowel Instrumentation, for Posterior Approach," Sofamor Danek, 1996.

Catalog from Cloward® Instruments, 1996.

White et al., *Clinical Biomechanics of the Spine*, J.B. Lippincott Co., 1978, White et al., 1990, 551–552.

Hochschuler et al, "Compressive Strength of Hollow, Allograft Bone Cylinders Proposed for Lumbar Interbody Fusion," NASS 8th Annual Meeting, Oct. 1993.

"MD–I™ and MD–II™ Custom Machined Cortical Dowels," University of Florida Tissue Bank, 1996.

"MD–III™ Threaded Cortical Dowel, Design Rationale and Surgical Technique," University of Florida Tissue Bank, 1997.

"Operative Treatment of Degenerative Cervical Disk Disease," Journal of the Southern Orthopaedic Association, 1996.

"Ray Threaded Fusion Cage, Surgical Technique Manual," Surgical Dynamics, 1996.

"Ray Threaded Fusion Cage," Surgical Dynamics, 1996.

"Surgeons First in Region to Use Lumbar Cage for Spinal Disc Disease," Hohmann Enterprises, 1996.

Heim et al, "The Treatment of Lumbar Degenerative Motion Segment Pain," Spinal Frontiers, Jun. 1997.

"Threaded Bone Dowel," Hohmann Enterprises, 1997.

Technical Monograph, Threaded Cortical Dowel, "Mechanical Characteristics and Evaluation," University of Florida Tissue Bank, 1996.

"Tyler Neurosurgeon Jon T. Ledlie, MD, Introduces Bone Dowel Procedures for East Texas–Area Back Pain Sufferers," Tyler Neurosurgical Assoc., 1998.

"Surgeons First in Region to Use Lumbar Cage for Spinal Disc Disease, " Hohmann Enterprises, 1996.

"Tyler Neurosurgeon Jon T. Ledlie, MD, Introduces Laparoscopic Procedure for East Texas Back Pain Sufferers," Tyler Neurosurgical Assoc., 1998.

"Vertigraft™ Textured Allograft Bone Graft," LifeNet, 1998.

"New Approaches to Spine Surgery," USC University Hospital Quarterly, vol. 10, No. 3, 1998.

Beadling, "FDA clears spinal cages for interbody lumbar fusion," Orthopedics Today, vol. 16, No. 10, Oct. 1996, pp. 24–25.

International Search Report, Application No. PCT/US98/08832, mailed Sep. 1, 1998.

* cited by examiner

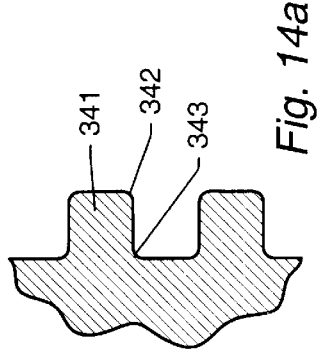
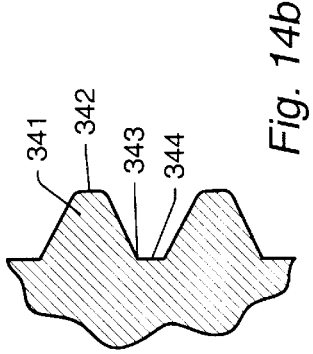
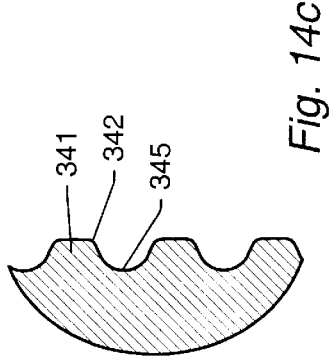
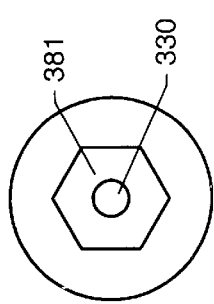
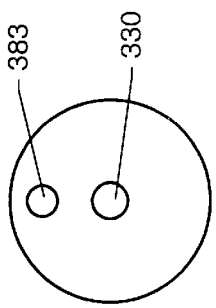
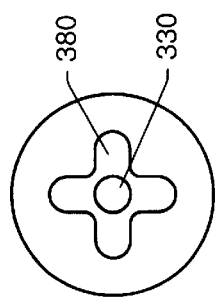
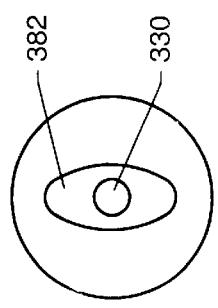
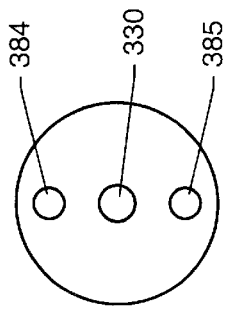

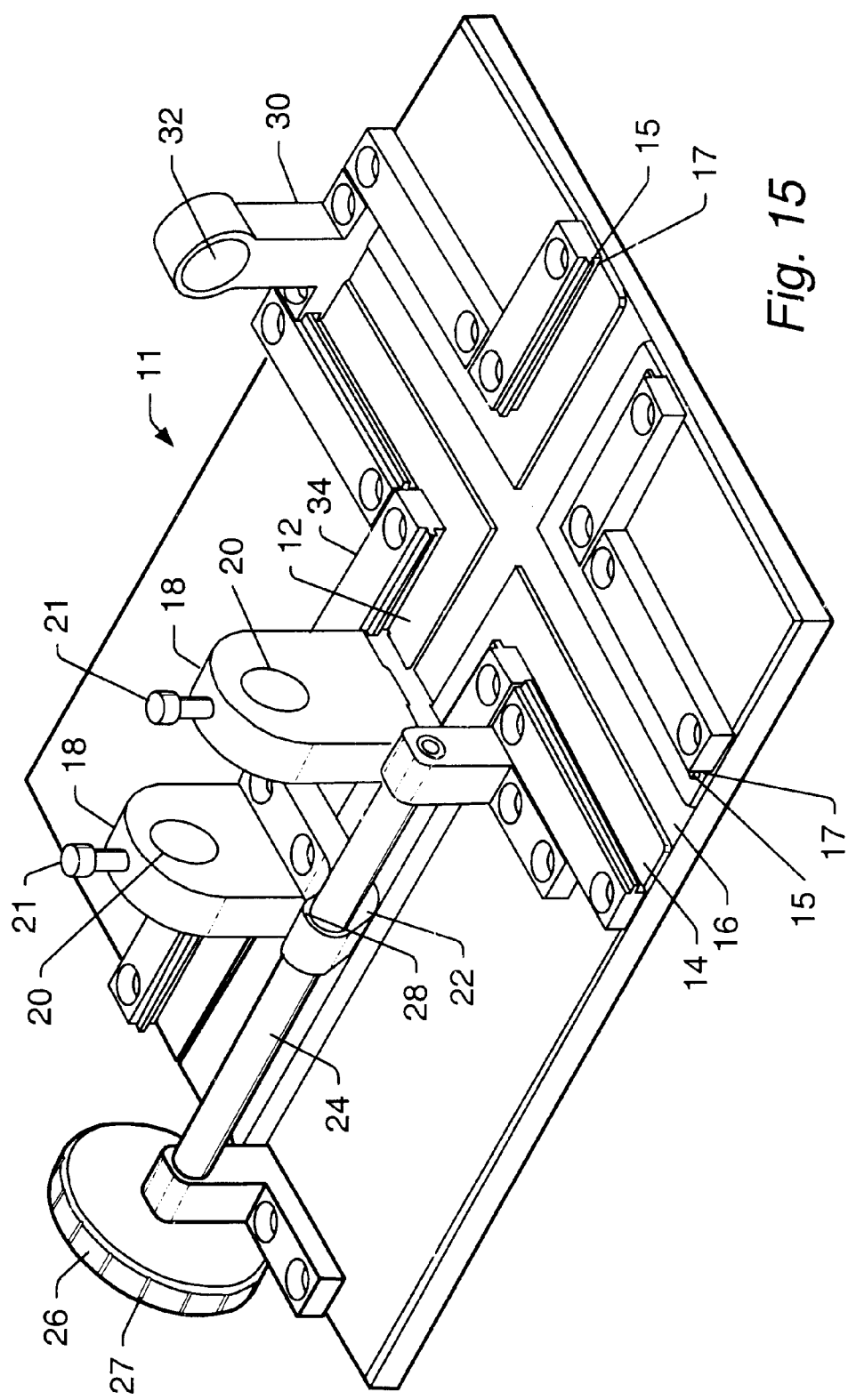

APPARATUS FOR MANUFACTURING A BONE DOWEL

This application is a continuation-in-part of U.S. patent application Ser. No. 09/298,269 filed on Apr. 23, 1999.

BACKGROUND OF THE INVENTION

1. Field of the Invention

The present invention is related to the field of bone dowels, and more specifically devices and method designed to be used (e.g., in a sterile setting) to manufacture a bone dowel for use in spinal surgery.

2. Description of the Related Art

Clinical spinal fusion procedures using bone graft have been used for decades. Anterior cervical interbody fusion using cylindrical smooth bone grafts as spacers was reported by several authors by the mid-1950's. In 1985, threaded cylindrical bone dowels were reported by Vich, eliminating the need to hammer the dowels in place. In the use of these dowels, a cylindrical bed was drilled in the appropriate intervertebral bodies and the graft was then screwed into the opening. Bone grafts could be attained from iliac crests as described by Cloward or using a Kiel-surgibone heterologous graft. Threaded dowels were prepared with a sterilized die or with a small lathe.

U.S. Pat. No. 5,814,084 describes cortical bone dowels derived from cortices of bone diaphyses that may have a chamfered insertion end. The dowels described in the '084 patent may also include a canal derived from the intramedullary space of a diaphysial bone that retains the natural architecture of that region of the bone, and which can be packed with cancellous bone. The background section of the '084 patent provides a discussion of the development of the art. The '084 patent is incorporated herein by reference.

SUMMARY OF THE INVENTION

A device for manufacturing a bone dowel may include a machine base with one or more tracks in a surface thereof. In some embodiments, at least one track may be perpendicular to at least one other track. In this configuration, the machine base may include at least one perpendicular intersection of two or more tracks. The device may also include a rotary cutting tool module, configured to hold a rotary cutting tool and to slide in a track in the machine base. The device may also include one or more modules for holding a dowel, preferably configured such that the modules are configured to slide in the tracks in both parallel and perpendicular orientation to a rotary cutting tool module disposed in a track during use, thus enabling an operator to perform various cutting, drilling and milling operations on a dowel.

As is described herein, one or more modules may slide in the tracks in perpendicular or parallel orientation to a cutting tool during use. Although embodiments are described in which a machine base includes two tracks in perpendicular orientation, a machine base may also include two, three, or more tracks perpendicular to one or more tracks that may be configured to hold a cutting tool module, for example. In this way, more than one dowel module may be disposed on the machine base simultaneously or even sequentially in different tracks as needed to contact one or more cutting tools.

In one embodiment, a device for manufacturing a bone dowel in which a rotary cutting tool may be held in an appropriate position, and a module holding a dowel may be moved relative to the cutting tool in order to contact the rotary tool and shape the dowel to the desired size and configuration is described. In other embodiments, both the cutting tool and the dowel are held in modules that slide in tracks for controlled positioning and machining of the dowel. Other embodiments may include only one track, and a module holding a bone dowel may contain a sliding member configured to allow the dowel to be moved perpendicular to the cutting tool held in a module mounted in the track.

The devices disclosed herein offer certain advantages over more conventional dowel manufacturing devices, such as lathes, in which a motor is connected to a shaft or other device configured to turn the dowel, and an operator then contacts the dowel with a knife, a gouge, or other stationary tool. Dowels made on such a device are typically machined to size in a clean room and then a number of different sizes are packaged and frozen. A surgeon typically thaws a number of different sizes of dowels so that one can be chosen during surgery to best fit the need of the patient. Unfortunately, the dowels that are not used cannot be re-frozen and must be discarded. The devices disclosed herein, in contrast, can be used in the operating room during surgery. The use of high speed rotary cutting tools is, in fact, routine in certain surgical procedures in operating rooms and the present device is adaptable to those rotary cutting tools. The present devices, then, may be sterilized and used in surgery to produce a dowel of the needed size from a dowel blank, after the surgeon has determined the needed size. This reduces waste of human tissue and unnecessary expense, since only the single dowel blank need be thawed, rather than a selection of pre-sized dowels.

The terms dowel, bone dowel, dowel blank, and bone portion are interchangeably used to describe a portion of bone that has been cut from donor bone and is ready for, or in the process of, being manufactured using the devices described herein. The terms dowel and bone dowel may be used to describe the finished product of the manufacturing process.

In certain embodiments, the modules for holding a dowel include a collet module, including a base configured to slide in a track and a collet configured to hold a dowel such that an end of the dowel may contact the cutting tool during use. A collet may be configured to hold a dowel by one end such that the opposite end may contact the cutting tool. As used herein, a dowel may typically be cylindrically shaped, such that the dowel is defined by two ends separated by the height of the dowel. The height may also be described as the long axis of the dowel, and the circumference of the long axis as the circumferential portion of the dowel. A collet module may be configured to hold a dowel parallel to the base of the module, or perpendicular to the base. As described herein, parallel means that the long axis of the dowel is parallel with the track in which the base is held during use. In some embodiments, a collet module may be useful to machine an end of a dowel smooth by moving a dowel in a track perpendicular to the rotary cutting tool until an end contacts the cutting tool burr. The dowel may then be manually rotated to achieve a smooth end. The collet module may also be useful for drilling a center hole in an end of a dowel by moving the dowel held in the collet module in parallel orientation to a drill bit mounted on a rotary cutting tool held in a rotary tool module. Alternately, a center hole may be drilled in an end of a dowel held in the collet module by moving a rotary tool module holding the drill bit or burr mounted on a rotary cutting tool in parallel orientation to the collet module.

The modules for holding a dowel may also include a vise module including a base configured to slide in a track and a vise configured to hold a dowel along the length thereof such that an end of the dowel may contact a cutting tool during use. In some embodiments, a vise module may include a base configured to be mounted in a track and a vise configured to hold a dowel mounted on a sliding member configured to slide on the base perpendicular to the track. A vise module may include an opposed pair of jaw members configured to move together to press against an object held between the jaw members. In some embodiments, vise modules may include a groove or indention in one or both jaw members configured to conform to the circumferential portion, or the sides of the long axis of a dowel. The module may preferably be configured to hold a dowel perpendicular to the base such that an end of the dowel is free to be machined during use. The vise module may also be configured to hold a dowel securely against a force resulting from a cutting tool traveling across the face of an end and from a force resulting from a drilling tool boring into the face of an end. The vise module may be useful in cutting a groove or slot into an end of a dowel. Such a groove or slot may be useful for interacting with a chuck coupled to a module during the manufacturing process, orienting a dowel during surgery, or for interacting with a tool used to insert the dowel into a spine. As such, a dowel held in the vise module may be moved in a track perpendicular to a cutting tool to machine such a groove or slot during use. The vise module may also be useful for drilling a center hole in an end of a dowel by moving a dowel held in the vise module in parallel orientation to a drill bit or burr mounted on a rotary cutting tool held in a rotary tool module. Alternately, a center hole may be drilled in an end of a dowel held in the vise module by moving a rotary tool module holding the drill bit or burr mounted on a rotary cutting tool in parallel orientation to the vise module.

A device for manufacturing a bone dowel may also include a threading module including a base configured to slide in a track, a dead center, and a chuck opposed to the dead center, configured to hold a dowel by the ends such that a cutting tool may contact the circumferential portion of the dowel during use. In certain embodiments, the chuck may be configured to hold the dowel by one end and may provide a mechanism for turning or rotating the dowel around its long axis. In other embodiments, a dead center is provided that may engage a center hole drilled in the opposite end of a dowel during a previous step in manufacture, and the dead center may be spring loaded to hold the dowel in the module during use. In some embodiments, a coil spring is used, but other spring configurations may also be used to bias the dead center toward the chuck of the module.

In certain embodiments, a device for manufacturing a bone dowel may include a support member coupled to the machine base in a track, wherein the support member includes a threaded opening. The support member may be disposed at an end of a track that is perpendicular to a track holding a cutting tool module, or it may be disposed anywhere in a perpendicular track, or even in parallel orientation to the cutting tool module. The threaded opening may be configured to engage a threaded projection included on certain modules, configured such that turning the threaded projection in the threaded opening is effective to move the module in the track. In this way an operator has better control of the module than is possible with a free-hand movement of the module. For example, a collet module may include a threaded projection configured to threadably mate with the threaded opening such that turning the threaded projection is effective to move the collet module in the track. The collet module may also include a knob coupled to the threaded projection configured so that turning the knob turns the threaded projection. The knob coupled to the threaded projection may include marks configured so that rotating the knob from one mark to a second mark relative to a fixed position moves the module a known distance in the track. In certain embodiments, a threading module may also include a threaded projection configured to threadably mate with the threaded opening such that turning the threaded projection is effective to move the threading module in the track, and to turn a dowel held in the threading module. In this way, an operator may make more than one pass with the threading module while maintaining the starting point and pitch in order to cut threads into a dowel. This embodiment makes it easy to return to the start of a thread. The pitch of the threaded opening also determines the pitch of the threads cut on a dowel.

The module for holding a rotary cutting tool as used in any of the described devices may be disposed in a track and may include an arm rigidly coupled to the module and configured to threadably engage a threaded rod. In certain embodiments, a threaded rod may be provided and disposed parallel to the track holding the rotary cutting tool module. In some embodiments, the rod is rotatable and may be held in one or more support members coupled to the machine base. In this configuration, turning the rod is effective to move the cutting tool module in the track. A knob may be coupled to the rod to aid an operator in turning the rod. The knob coupled to the rod may include marks configured so that rotating the knob from one mark to a second mark relative to a fixed position moves the rotary cutting tool module a known distance in the track. Any of the devices described herein may further include a high speed rotary cutting tool.

Described herein are also methods of manufacturing a bone dowel. Methods may include: providing a machine base including two or more tracks, wherein at least one track is perpendicular to at least one other track; providing a rotary cutting tool module in a first track and further providing a rotary cutting tool held in the module; providing one or more modules for holding a dowel, wherein the modules are configured to slide in the tracks in both parallel and perpendicular orientation to the first track; providing a bone dowel; moving the bone dowel past the cutting tool and in contact with a burr mounted on the cutting tool by sliding a module holding the dowel past the cutting tool when the module is in a second track, perpendicular to the first track, by sliding a module toward the cutting tool when the module is in the first track, or by sliding a sliding member of a module for holding a dowel past the cutting tool while the module is in the first track; moving a burr mounted on a cutting tool to contact the dowel by sliding a module holding the cutting tool toward a module holding the dowel when the module holding the dowel is in the first or second track. In some embodiments, the modules for holding a dowel may include a collet module including a base configured to slide in a track and a collet configured to hold a dowel such that an end of the dowel may contact the cutting tool during use; a vise module including a base configured to slide in a track and a vise configured to hold a dowel along the length thereof such that an end of the dowel may contact a cutting tool during use; and a threading module including a base configured to slide in a track, a dead center, and a chuck opposed to the dead center, configured such that a dowel held in the threading module may contact a cutting tool while rotating around the long axis of the dowel during use.

Methods may also include providing a support member coupled to the machine base in a track, wherein the support member includes a threaded opening, and may further include providing a support member including a threaded opening coupled to the machine base in a track, wherein the collet module includes a threaded projection configured to threadably mate with the threaded opening such that turning the threaded projection is effective to move the collet module in the track, and wherein the vise module includes a threaded projection configured to threadably mate with the threaded opening such that turning the threaded projection is effective to move the vise module in the track. In addition, some embodiments may include providing a support member including a threaded opening coupled to the machine base in a track, and wherein the threading module includes a threaded projection configured to threadably mate with the threaded opening such that turning the threaded projection is effective to move the threading module in the track, and to turn a dowel held in the threading module. In the practice of some embodiments, the module for holding a rotary cutting tool may be disposed in a track and include an arm rigidly coupled to the module and configured to threadably engage a threaded rod, wherein the rod may be disposed parallel to the track and may be rotatable in one or more support members coupled to the machine base such that turning the rod may be effective to move the module in the track.

Some embodiments of manufacturing a bone dowel as described herein may also include placing a collet module in a second track, perpendicular to a first track, and securing the bone dowel in the collet module; mounting a cutting tool burr on the cutting tool; moving the cutting tool module to position the cutting tool burr parallel with the end of the dowel; moving the collet module to contact the cutting tool burr effective to smooth the first end of the dowel; repositioning the dowel in the collet and moving the collet module to contact the cutting tool burr effective to smooth the second end of the dowel; mounting a bit in the cutting tool; moving the collet module to the first track; moving the collet module to contact the cutting tool bit effective to drill a centered hole in the end of the dowel; repositioning the dowel in the collet and moving the collet module to contact the cutting tool burr effective to drill a centered hole in the opposite end of the dowel.

The methods may also include: mounting a cutting tool burr in the cutting tool; placing a vise module in a track perpendicular to the first track; securing the dowel in the vise module; moving the cutting tool module to position the cutting tool burr parallel with the end of the dowel; moving the vise module past the cutting tool effective to machine a groove in an end of the dowel. The methods may also include mounting a threading burr on the cutting tool; placing a threading module in a track perpendicular to the first track; mounting the dowel in the threading module; positioning the modules so that the burr contacts the dowel near one end thereof; and simultaneously turning the dowel and sliding the threading module past the cutting tool effective to thread the dowel.

Other embodiments of manufacturing a bone dowel may include placing a vise module in a first track, and securing the bone dowel in the vise module; mounting a cutting tool burr on the cutting tool; moving the cutting tool module to position the cutting tool burr parallel with the end of the dowel; moving the vise module to contact the cutting tool burr effective to smooth the first end of the dowel; repositioning the dowel in the vise and moving the vise module to contact the cutting tool burr effective to smooth the second end of the dowel; mounting a bit in the cutting tool; moving the vise module to contact the cutting tool bit effective to drill a centered hole in the end of the dowel; repositioning the dowel in the vise and moving the vise module to contact the cutting tool burr effective to drill a centered hole in the opposite end of the dowel; mounting a cutting tool burr in the cutting tool; moving the cutting tool module to position the cutting tool burr offset from the center of the end of the dowel mounted in the vise module; moving the vise module towards the cutting tool effective to machine a starting hole in an end of the dowel; moving the dowel mounted in the vise module perpendicular to the cutting tool module effective to machine a groove on the end of the dowel from the starting hole, across the center of the dowel, to a position opposed to the starting hole. The methods may also include mounting a threading burr on the cutting tool; placing a threading module in a track perpendicular to the first track; mounting the dowel in the threading module; positioning the modules so that the burr contacts the dowel near one end thereof; and simultaneously turning the dowel and sliding the threading module past the cutting tool effective to thread the dowel.

Also disclosed herein are methods of manufacturing a device for manufacturing a bone dowel, including: manufacturing a machine base including two or more tracks, wherein at least one track is perpendicular to at least one other track; manufacturing a rotary cutting tool module, wherein the module is configured to hold a rotary cutting tool and to slide in a track; and providing one or more modules for holding a dowel, wherein the modules are configured to slide in the tracks in both parallel and perpendicular orientation to a rotary cutting tool module disposed in a track during use. In some embodiments, the modules for holding a dowel may include a collet module including a base configured to slide in a track and a collet configured to hold a dowel such that an end of the dowel may contact the cutting tool during use; a vise module including a base configured to slide in a track and a vise configured to hold a dowel along the length thereof such that an end of the dowel may contact a cutting tool during use; and a threading module including a base configured to slide in a track, a dead center, and a chuck opposed to the dead center, configured such that a dowel held in the threading module may contact a cutting tool while rotating around the long axis of the dowel during use.

The present disclosure also includes bone dowels manufactured by the methods and/or utilizing the devices described herein. Such dowels may also include dowels in which the canal formed by the intramedullary space has been improved by the removal of cancellous bone to promote better bone grafting of a dowel to the adjacent vertebrae.

Embodiments of a bone dowel as described herein may include a slot machined in an end of the bone dowel so that the perimeter of the slot does not substantially violate the outer edge of the end of the bone dowel. The slot may be useful for interacting with a chuck coupled to a module used to hold or rotate the bone dowel during the manufacturing process, orienting a dowel during surgery, or for interacting with a tool used to insert the dowel into a spine. In some embodiments, the slot may be completely enclosed by the bony material at the end of the dowel and may be between 1 and 1.5 millimeters deep. In other embodiments, the slot may have rounded corners. In yet other embodiments, there may be a plurality of slots in the end of the dowel. The slot may be in a number of shapes, including, but not limited to, a rectangle with rounded corners, a cross, a hexagon, and an oval.

Some embodiments of a bone dowel may also include threads with radiused edges at the top of the threads and radiused corners at the base of the threads, and with substantially flat surfaces between the edges and corners. The term radiused as used herein describes a thread profile wherein the angular edges and corners of the threads have been smoothed to a substantially circular form. In some embodiments, the threads may be rounded into a sinusoidal shape. The term sinusoidal as used herein describes a thread profile that is continuously curved or radiused at all points. In other embodiments, the threads may have radiused edges at the top of the threads and angular corners at the bottom of the threads.

In some embodiments of a bone dowel a hole is drilled in an end of the dowel. A bone dowel may include a hole drilled in both ends of the dowel. The holes may be substantially centered on the ends of the dowel. The holes may include internal threading. The holes may extend from the ends of the dowel to the canal formed by the intramedullary space. In an embodiment, the holes may have a diameter approximately 10% that of the bone dowel, and the holes may be drilled through both ends of the bone dowel into the canal space, with internal threading in at least one of the hole extending about 50% from the slotted end of the bone dowel to the inner surface.

A bone dowel may be manufactured from sections of human long bones, with the intramedullary space oriented so as to form the canal of the bone dowel, and the cancellous bone material removed from the canal with, for example, a burr or file. Alternatively, a bone dowel may be manufactured from the long bones of other species, for example bovine, sheep, and pig, wherein the long bones are of sufficient dimensions to produce bone dowels of the required sizes. In another embodiment, a bone dowel may be manufactured from bones with sufficient dimensions and strength to produce bone dowels of the required size but lacking a natural canal such as the intramedullary space of a long bone. In these embodiments, the canal may be machined through the bone dowel.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 13a depicts the first end of a bone dowel with a cross slot.

FIG. 13b depicts the first end of a bone dowel with a hexagonal slot.

FIG. 13c depicts the first end of a bone dowel with an oval slot.

FIG. 13d depicts the first end of a bone dowel with a single slot offset from the centered hole.

FIG. 13e depicts the first end of a bone dowel with a multiplicity of slots.

FIG. 14a depicts bone dowel threads with rounded edges and corners.

FIG. 14b depicts rectangular bone dowel threads with rounded top edges and bottom corners.

FIG. 14c depicts trapezoidal bone dowel threads with rounded top edges.

FIG. 15 depicts another embodiment of a machine base.

DETAILED DESCRIPTION

Figure 1:
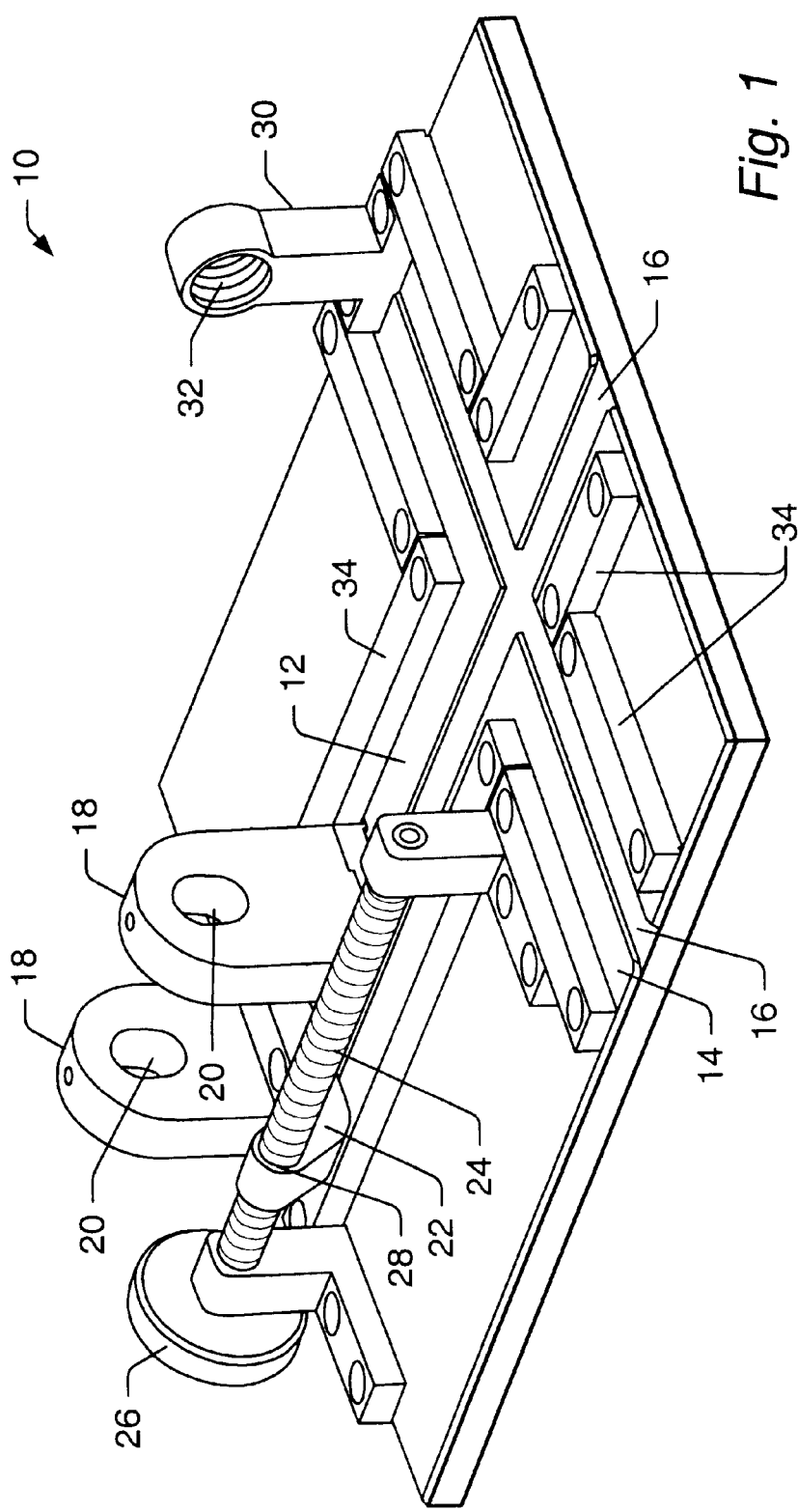
FIG. 1 depicts a machine base without cutting tools or modules.

An embodiment of a machine base 10 without cutting tools or modules is shown in FIG. 1. The machine base shown includes perpendicular tracks defined by rails 34, including a cutting tool track 12 and a track for the working modules 14 that intersect to form a cross shape. Both tracks include a groove 16 to guide the motion of the various modules in the tracks. The machine base as shown in FIG. 1 also includes a cutting tool module 18 configured to hold a standard high speed cutting tool. Such tools may be obtained from Dremel of Racine, Wis., for example. In the embodiment shown, the tool lies horizontally in the openings 20. The cutting tool module 18 is shown connected by an arm member 22 to a bar or rod 24. The bar 24 is shown coupled to a knob 26. In the embodiment shown, bar 24 may be threaded and may be configured to mate with threads in an opening 28 in the end of arm member 22. In this configuration, turning knob 26 is effective to move the cutting tool module 18 along the track 12, and to thus move the cutting tool toward or away from a dowel during use. The embodiment shown also includes a support member 30 having an opening 32 therethrough, which may in certain embodiments be a threaded opening configured to accept an extension, or a threaded extension of a working module during use.

FIG. 15 shows another embodiment of a machine base 11 without cutting tools or modules. In this and other embodiments, the rails 34 may include a projection 15 and a groove 17 to slidably mate with a complementary groove and projection on a module base. The cutting tool module 18 may also include screws 21 for securing a high speed cutting tool (not shown) in openings 20. Also, the knob 26 coupled to the bar 24 may include marks 27 configured so that rotating the knob from one mark to a second mark relative to a fixed position moves the cutting tool module 18 a known distance along the track 12. In some embodiments of a machine base, marks may be disposed along the tracks of the base so that the movement of modules along the tracks may be measured using the marks. Marks on the knob and along the tracks may be useful in performing precise machining of a bone dowel during the manufacturing process.

Figure 2:
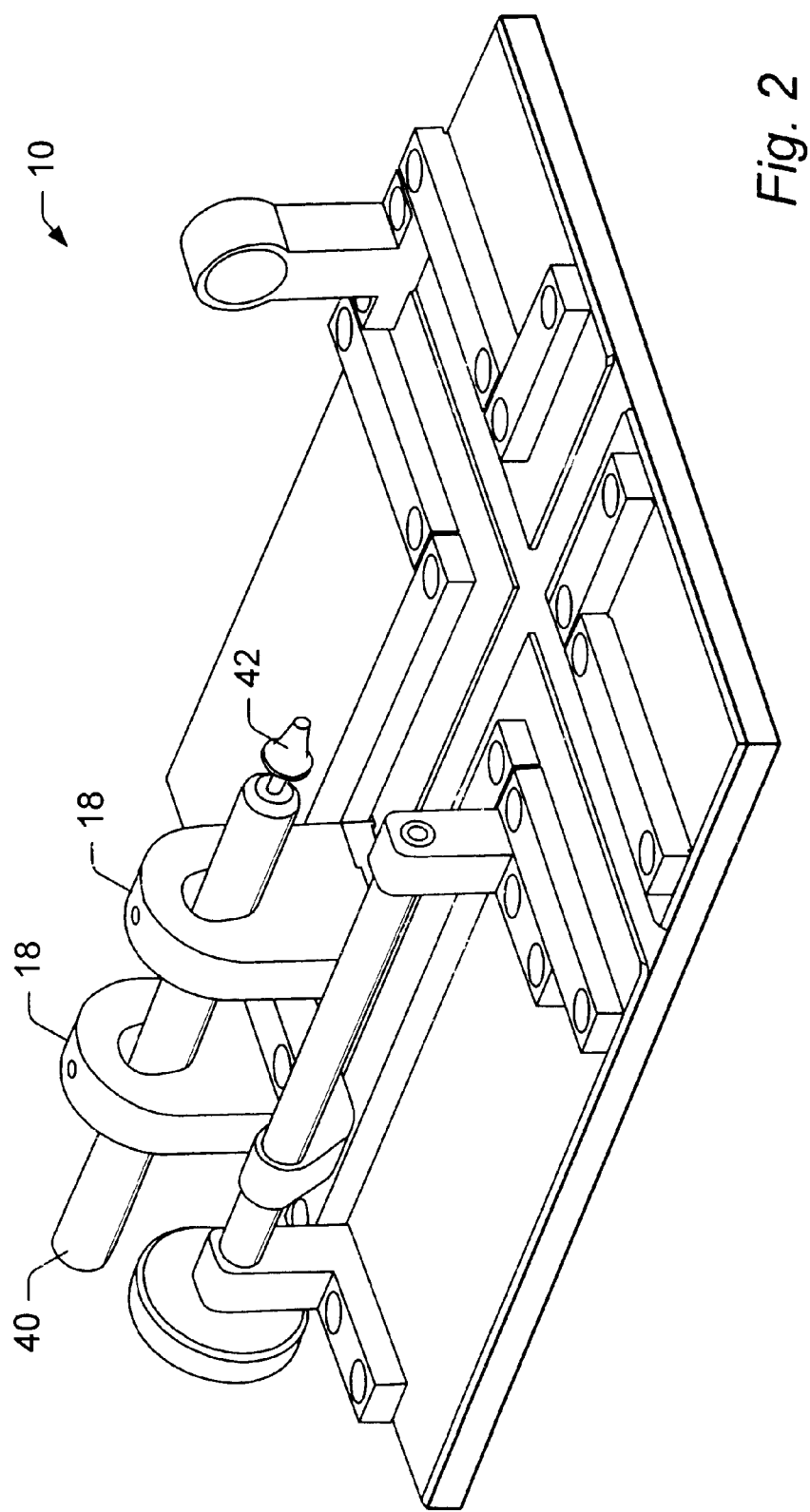
FIG. 2 depicts a machine base with a cutting tool.

A machine base 10 with a cutting tool 40 held in the cutting tool module 18 is shown in FIG. 2. Typically, the cutting tool 40 is connected to a switched motor by a cable (not shown) configured to turn a shaft in the tool 40 at high speed. Shown mounted on the cutting tool 40 is a burr or bit 42 for working the dowel.

Figure 16:
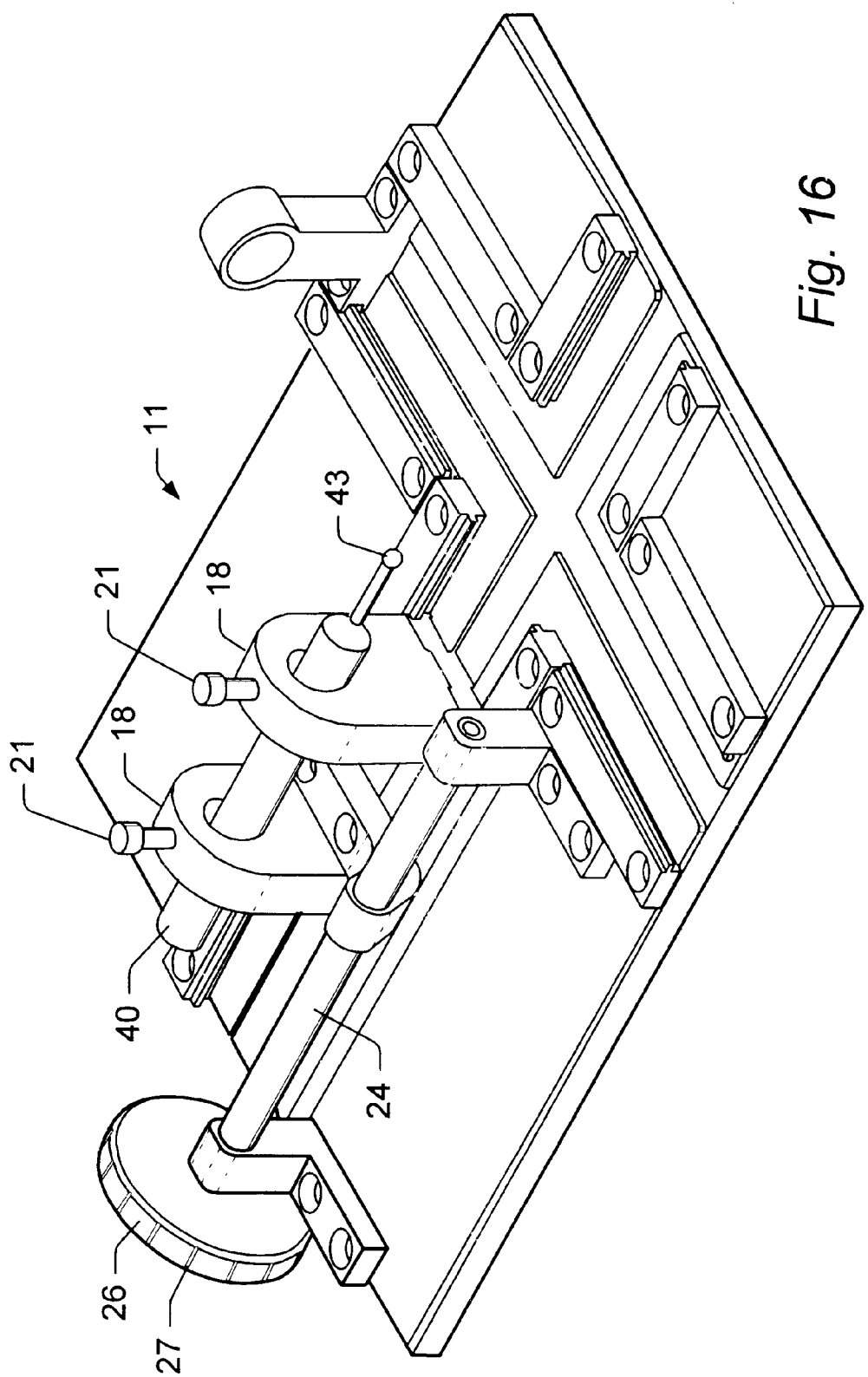
FIG. 16 depicts another embodiment of a machine base with a cutting tool.

Another embodiment of a machine base 11 with a cutting tool 40 held in the cutting tool module 18 is shown in FIG. 16. In this and other embodiments, the cutting tool module 18 may include screws 21 for securing a high speed cutting tool 40 in openings 20. Shown mounted on the cutting tool 40 is an embodiment of a burr or bit 43 for working the dowel. In some embodiments, the knob 26 coupled to the bar 24 may include marks 27 configured so that rotating the knob from one mark to a second mark relative to a fixed position moves the cutting tool module 18 holding the cutting tool 40 a known distance along the track 12.

Figure 3:
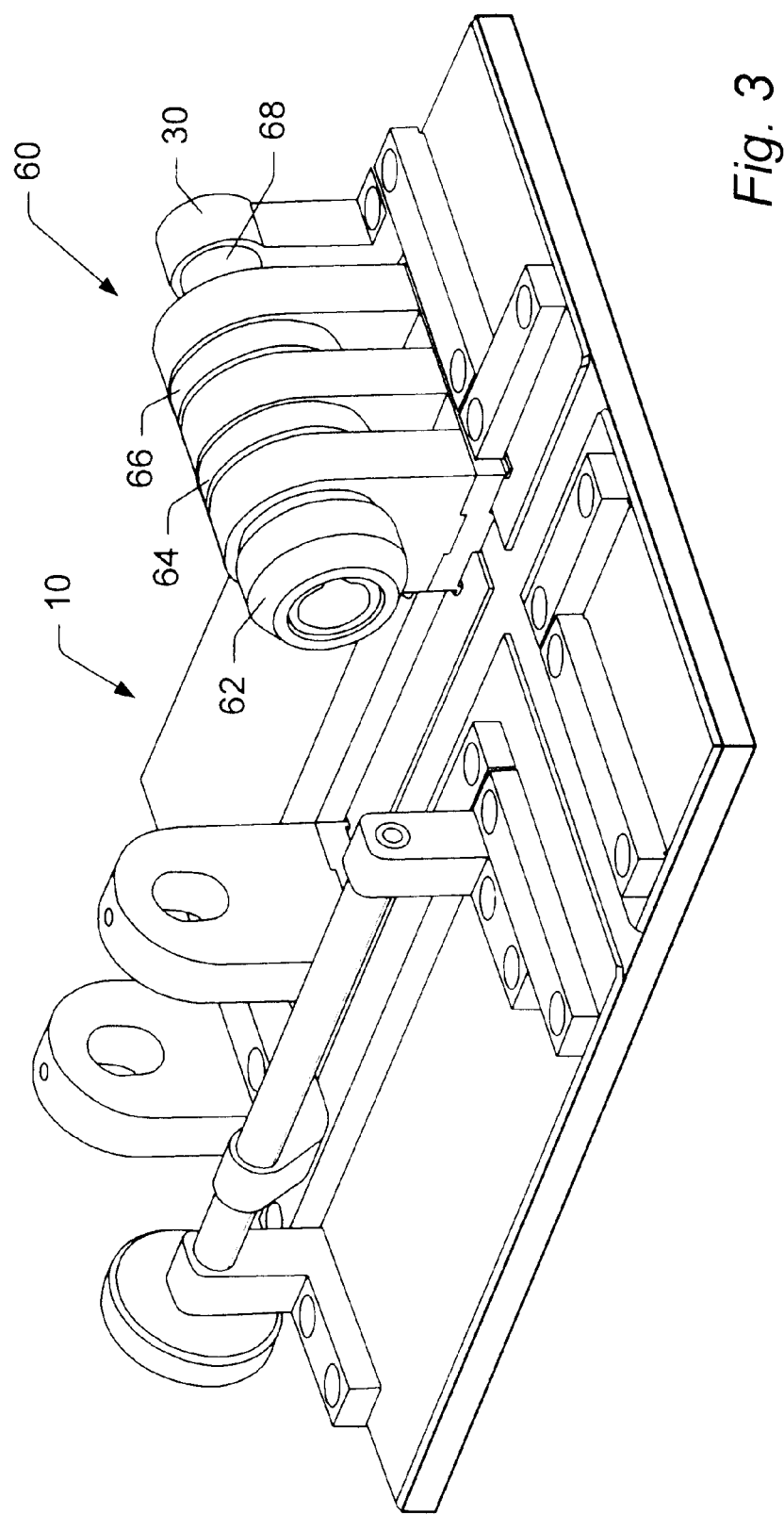
FIG. 3 depicts a machine base with a collet module in the perpendicular position.
Figure 7:
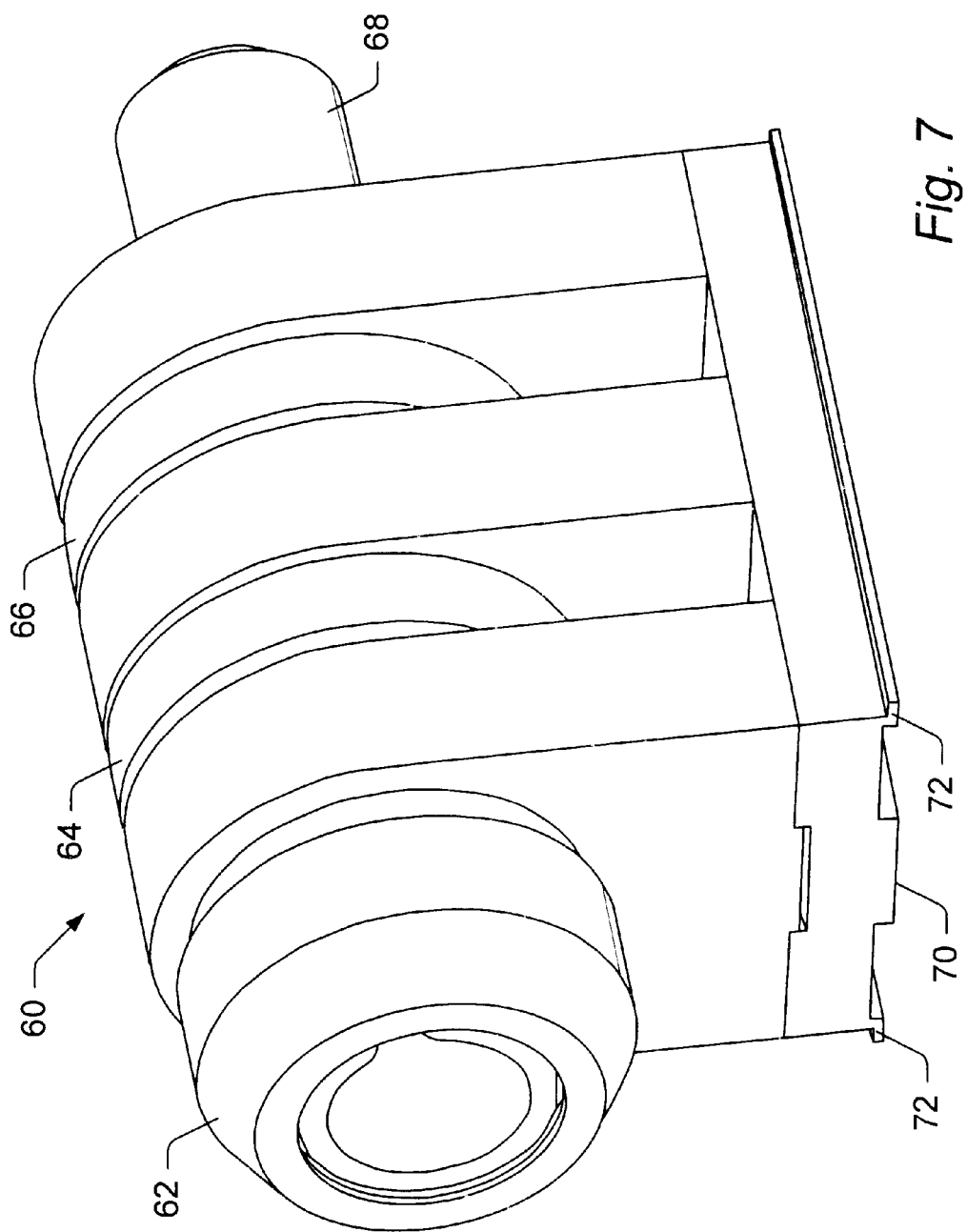
FIG. 7 depicts a collet module.

A machine base 10 with a collet module 60 in the perpendicular position is shown in FIG. 3. A collet module 60 is also shown in isolation in FIG. 7. The collet module includes a collet 62 configured to hold a bone dowel. A knob 64 may be connected to the collet 62 such that turning the knob turns the collet 62 and thus a dowel held in the collet 62. A second knob 66 may be connected to an extension 68, preferably a threaded extension. As shown in FIG. 3, extension 68 may be received by support member 30, such that when the extension 68 and the opening 32 include mating threading, turning of knob 66 is effective to move the collet module 60 along the track 14, thus moving a dowel held in collet 62 perpendicular to a cutting tool 40 during use. Also shown in FIG. 7, the bottom of the collet module may include a projection 70 configured to ride in grooves 16 within tracks 12 and 14 of machine base 10. Also shown are flanges 72, configured to mate with rails 34. This configuration allows precise, controlled movement of the modules through the tracks.

Figure 4:
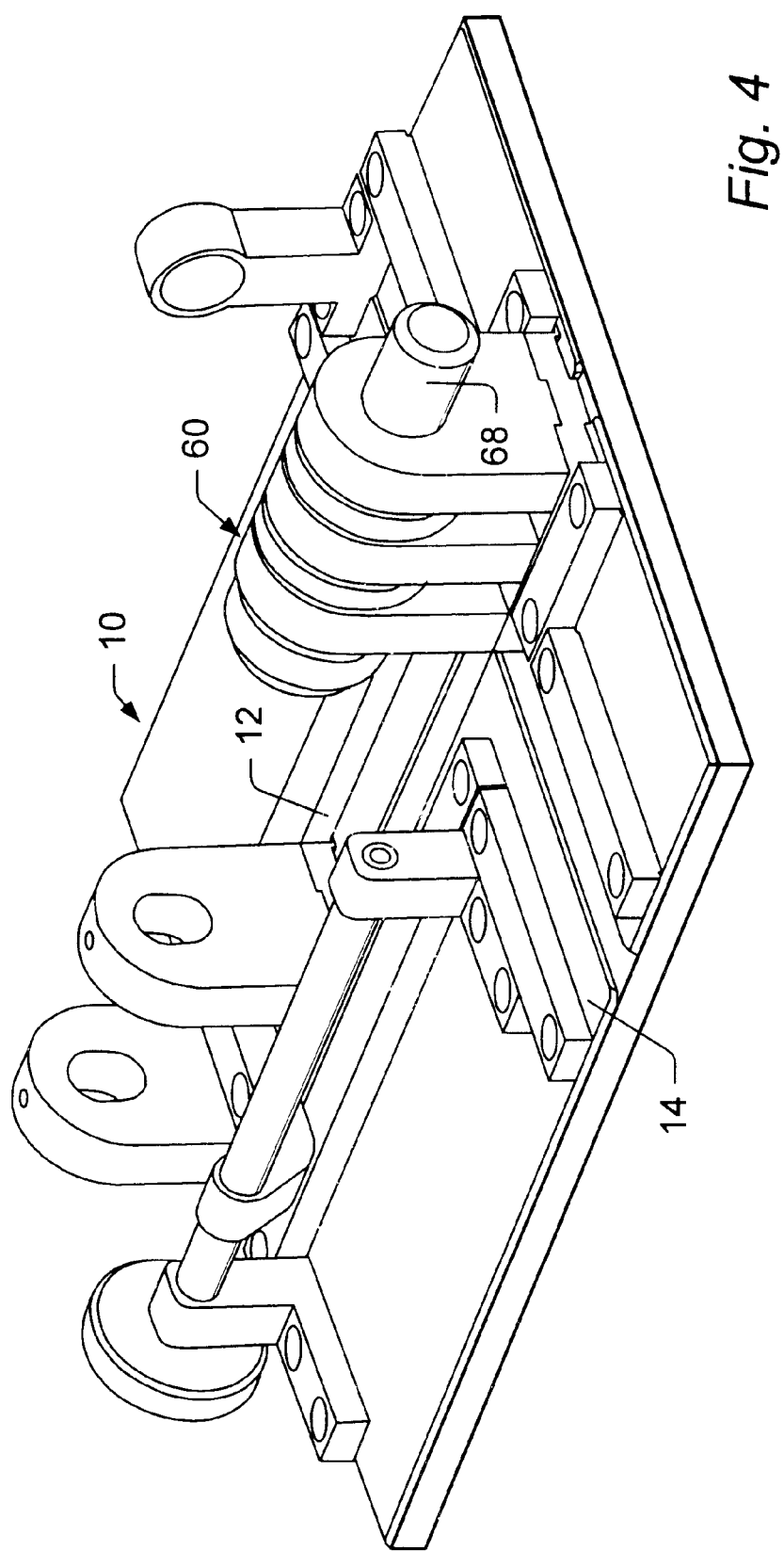
FIG. 4 depicts a machine base with a collet module in the parallel position.

During the manufacture of a bone dowel, the collet module is most useful for holding a dowel by one end while smoothing and drilling holes in the opposite end of the dowel. For example, a bone dowel may be held by one end in the collet with the collet module in the perpendicular orientation. Initially, the collet module may be positioned next to the support member, so that the dowel does not extend over the cutting tool track 12. The cutting tool module may be positioned such that the burr may extend over the track 14. During use, the cutting tool motor may be turned on so that the burr is turning at high speed. By turning the knob 66 in the appropriate direction, the collet module 60 moves along the track 14 (perpendicular) until the dowel contacts the cutting tool burr, thus smoothing the end of the dowel. The collet module 60 may also be placed in the cutting tool track 12 (parallel orientation) such that the dowel may be pushed by hand directly into the turning burr or bit thus drilling a hole in the end of the dowel. FIG. 4 depicts a machine base 10 with a collet module 60 in the parallel orientation as described. In the parallel orientation, the collet module 60 is preferably pushed along the track 12 by free hand, as the extension 68 is typically not engaged with a threaded opening.

Figure 5:
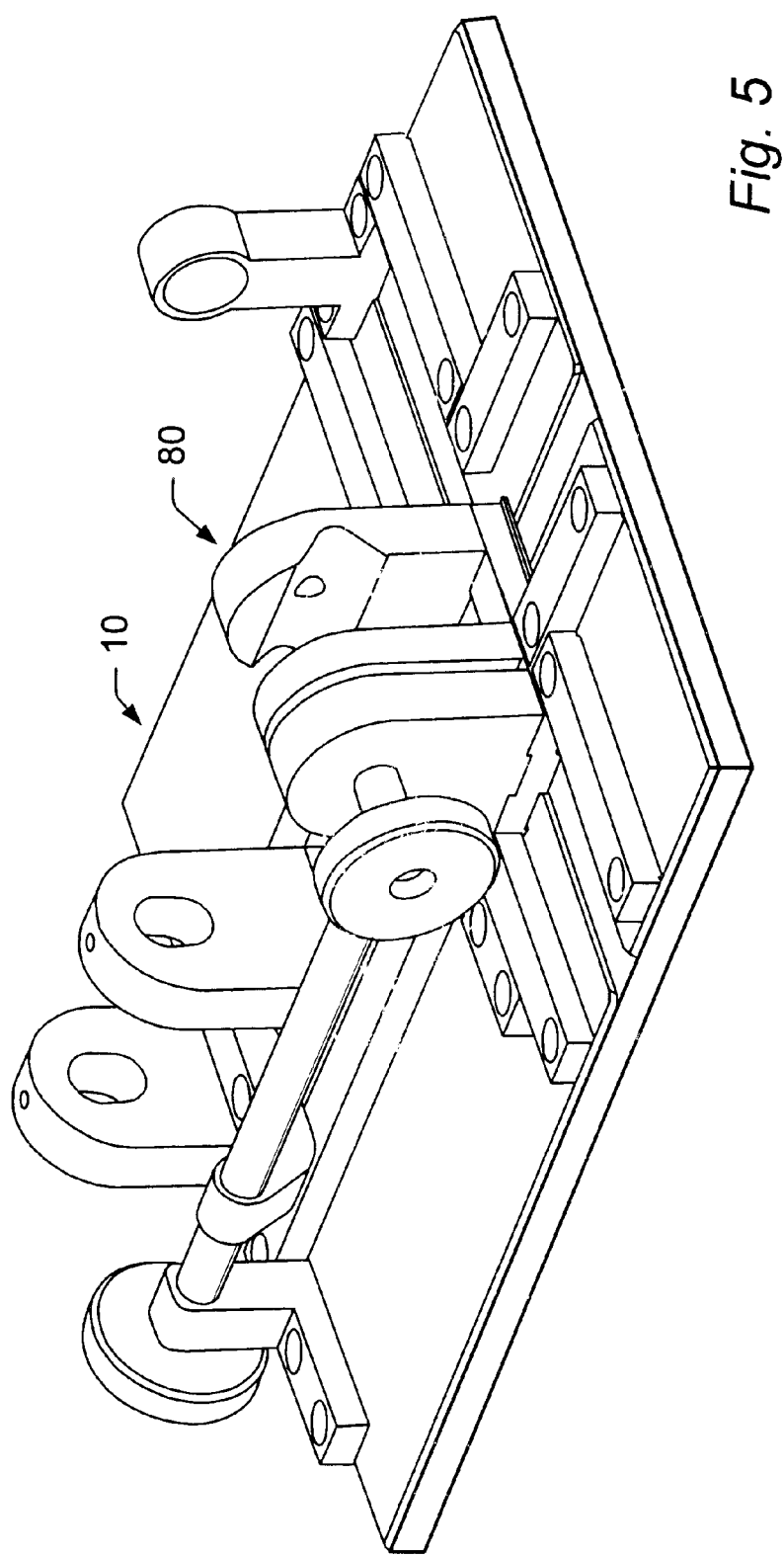
FIG. 5 depicts a machine base with a vise module.
Figure 8:
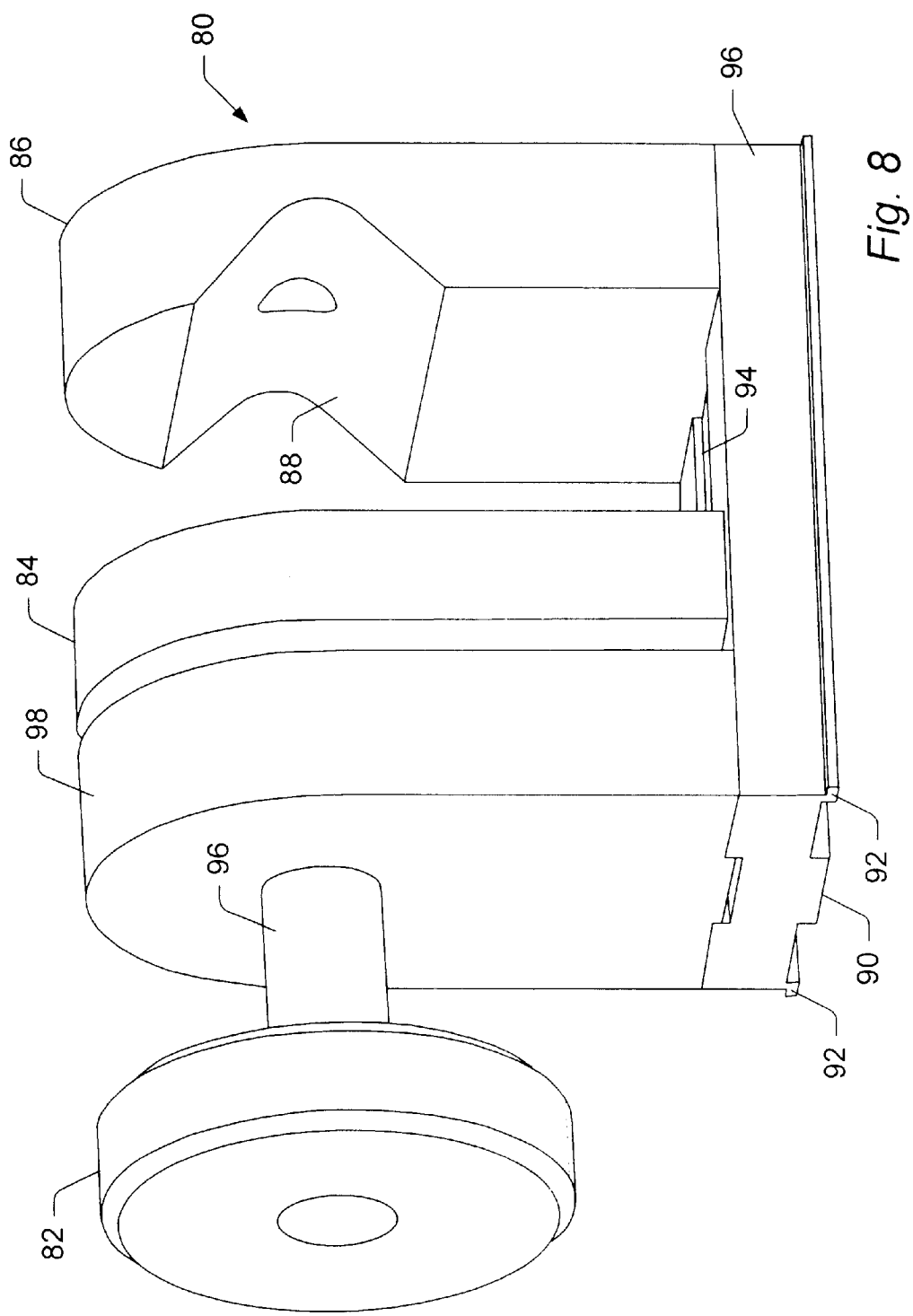
FIG. 8 depicts a vise module.

A machine base 10 with a vise module 80 is shown in FIG. 5. An example of a vise module 80 is shown in isolation in FIG. 8. The vise module 80 may be configured to hold a dowel so that an end of the dowel may be machined. Referring to FIG. 8, a vise module 80 may include a bottom as described for the collet module 60, including a projection 90 configured to ride in grooves 16 within tracks 12 and 14 of machine base 10. Also shown are flanges 92, configured to mate with rails 34. The bottom or base 96 of the vise module 80 may also include a track 94 on its top for a moveable vise jaw 84. The vise module 80 may also include a stationary vise jaw 86 that provides a groove 88 configured to hold one side of a dowel. The vise module 80 may also include a knob 82 connected to the moveable vise jaw 84 by a rod 96. Support member 98 may provide a threaded opening, with threads that mate with threads on rod 96 such that turning knob 82 threads the rod 96 through the support member 98, thus moving the moveable jaw 84 until it contacts the stationary jaw 86, or a dowel held between the jaws of the vise. During use, a dowel may be held in the vise by force applied through turning of knob 82.

During manufacture of a bone dowel as described herein, the vise module 80 may be placed on the machine base 10 in the perpendicular orientation as shown in FIG. 5. A dowel may be placed in the vise and secured by turning knob 82 until the pressure of the jaws is sufficient to hold the dowel. Typically a cutting tool burr configured to produce a straight sided groove or slot is mounted on the cutting tool and the tool is turned on. The vise module may then be moved past the cutting tool burr so that a groove or slot is cut in the end of the dowel. The cutting tool module may then be moved closer to the vise module and the process repeated to deepen the groove or slot as necessary. During surgical implantation of a dowel, such a groove or slot is useful to mate with a driver apparatus. The groove or slot may also be useful during the manufacturing process to interact with a chuck.

Figure 17:
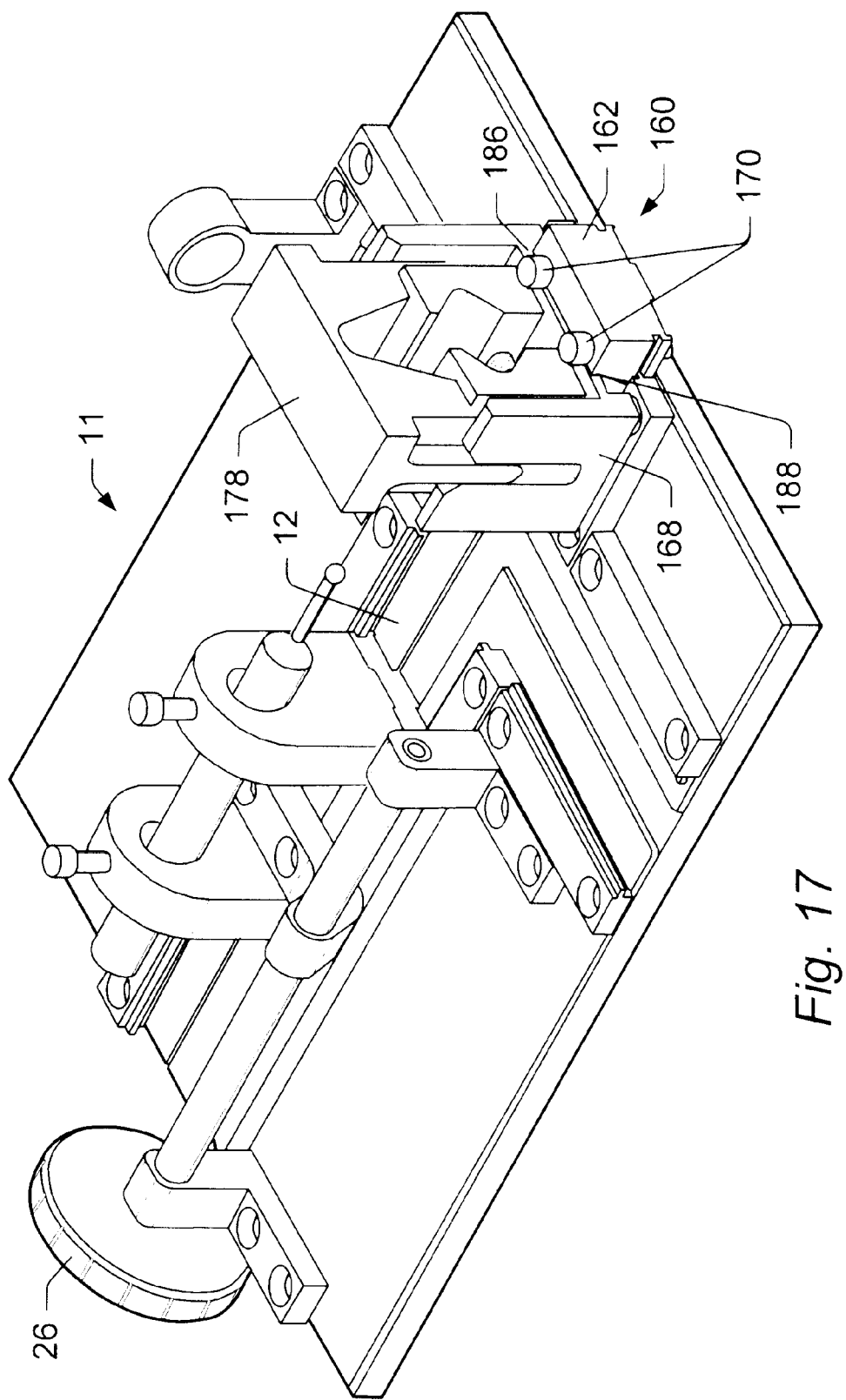
FIG. 17 depicts another embodiment of a machine base with a vise module.
Figure 19:
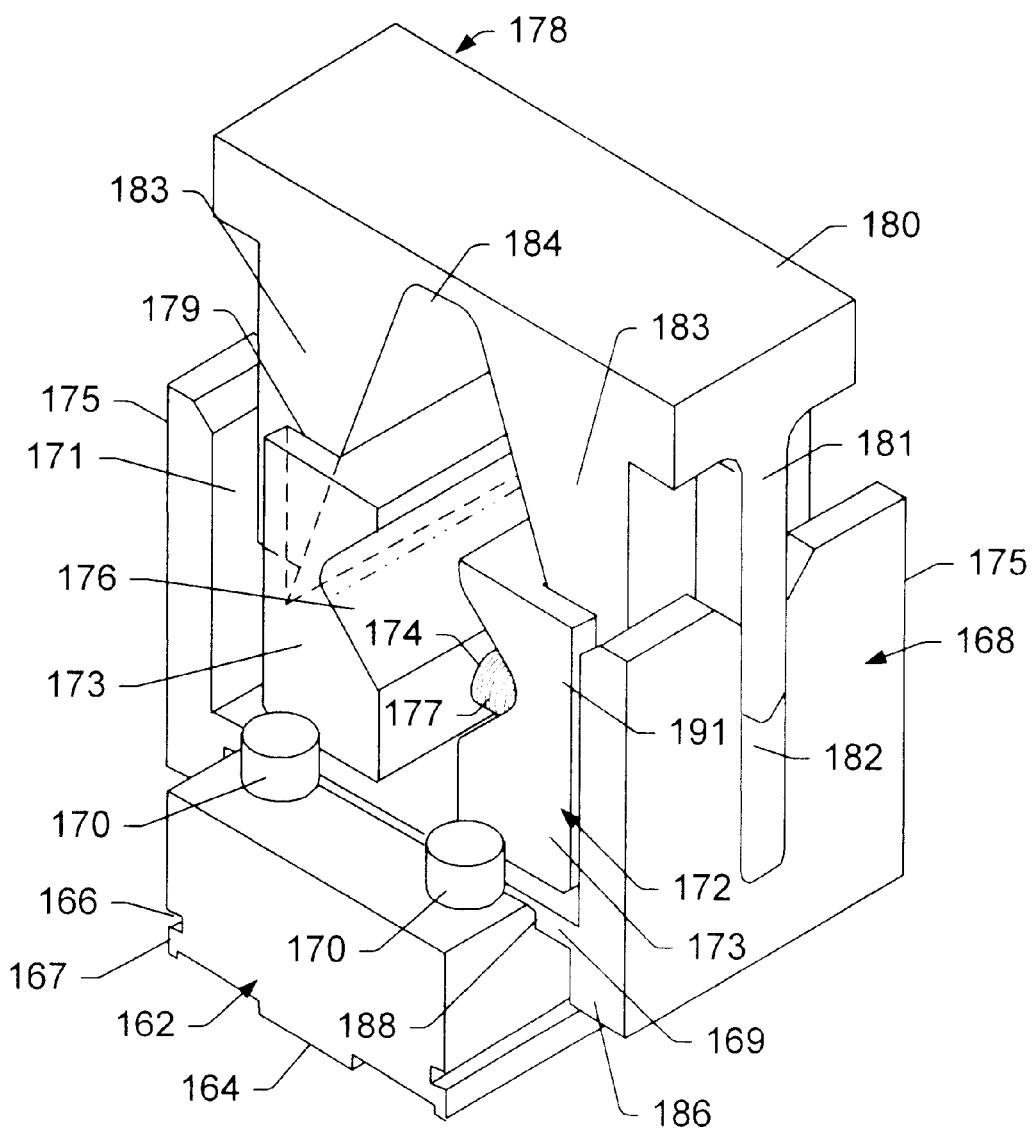
FIG. 19 depicts another embodiment of a vise module.

FIG. 17 shows another embodiment of a machine base 11 with a vise module 160. One embodiment of a vise module 160 is shown in FIG. 19. The vise module 160 may be configured to hold a dowel so that an end of the dowel may be machined. Referring to FIG. 19, the vise module may include a base member 162, a frame member 168, a clamp member 172, and a press member 178. The bottom of base member 162 may include a projection 164 configured to ride in grooves 16 within tracks 12 and 14 of machine base 11. Also shown are grooves 166 and projections 167, configured to slidably mate with complementary projections 15 and grooves 17 on rails 34 of machine base 11. This configuration allows precise, controlled movement of the module through the tracks. Base member 162 may also include a groove 188 to mate with a frame member base 169 of frame member 168. One or more retaining screws 170 may be located on each end of base member 162. The retaining screws 170 may be configured to overlap frame member base 169 so that tightening of the screws 170 in base member 162 fixably secures frame member 168 in groove 188. Loosening of the screws 170 in base member 162 may allow frame member 168 to slide in groove 188. Both sides 175 of frame member 168 may include stops 186 configured to limit the movement of frame member 168 within groove 188 by contacting the sides of base member 162 when frame member 168 has reached its limit of travel. The ability to mount frame member 168 securely to base member 162 by tightening the retaining screws 170, and also to mount frame member 168 loosely to base member 162 by loosening the retaining screws 170, provides two advantages. First, vise module 160 may be placed in the cutting tool track 12 parallel to a cutting tool module and remain there while in use; the sliding action of frame member 168 makes it unnecessary to move vise module 160 into a perpendicular track. Second, vise module 160 may be used to perform the functions of both the previously described vise module 80 and collet module 60 in the manufacturing process.

Frame member 168 may also include a slot 171 bounded by two sides 175. The two sides 175 of frame member 168 may include slots 182. Press member 178 may include a top 180, a slot 184 enclosed by two arms 183 with angled inside edges, and projections 181 on arms 183. Press member 178 may slidably mate with frame member 168, with the arms 183 of frame member 178 fitting inside the sides 175 of frame member 168, and the projections 181 on the arms 183 fitting inside the slots 182 in the sides 175 of frame member 168. Clamp member 172 may include two jaws 173 and a spring device 177. Each jaw 173 may include on one side a hole 174 configured to receive an end of spring device 177 and a groove 176 configured to hold one side of a dowel. In some embodiments, a surface of groove 176 may include roughening to provide additional friction to a dowel held in groove 176. Examples of roughening that may be applied to the surface of groove 176 include, but are not limited to, a matte finish, a diamond pattern, horizontal grooving, and vertical grooving. An angled slot 179 may extend substantially down the side of each jaw 173 opposite the hole 174 and groove 176; the slot may be configured to receive an arm 183 of press member 178. The angled slots 179 of the jaws 173 may be angled at a degree complementary to the angled inside edges of the arms 183 of press member 178.

An embodiment of a vise module 160 as shown in FIG. 19 may be assembled by first mounting a frame member 168 on a base member 162 by inserting the frame member in groove 188 and inserting retaining screws 170 into the base member 162. Jaws 173 may then be coupled to each end of a spring device 177 to create a clamp member 172. Clamp member 172 may then be inserted into a slot 171 of frame member 168. A press member 178 may then be inserted over clamp member 172, with the two arms 183 fitting between the angled slots 179 of the jaws 173 and the sides 175 of frame member 168, and the projections 181 on the arms 183 of press member 178 fitting into the slots 182 in the sides 175 of frame member 168. Vise module 160 may be configured so that, in a static state with no force being applied to the top 180 of press member 178, the two arms 183 of press member 178 will extend partially into the gap between the angled slots 179 of the jaws 173 and the sides 175 of frame member 168. Applying force to the top 180 of press member 178 may cause the angled inside surfaces of the arms 183 of press member 178 to apply a wedging force to the angled slots 179 of the jaws 173. The effect of the wedging force applied by the press member 178 to the jaws 173 of clamp member 172 is to cause the jaws 173 to move toward each other, compressing spring device 177. As more force is applied, the jaws 173 continue to move toward each other until stopped by the limit of compression of spring device 177, by a dowel held in the grooves 176 of the jaws 173, or by the jaws 173 contacting each other. Release of the downward force applied to press member 178 causes spring device 177 to decompress. The decompression of spring device 177 forces the jaws 173 to move apart. The outward motion of the jaws 173 applies a wedging force from the angled slots 179 of the jaws 173 to the angled inside surfaces of the arms 183 of press member 178. The effect of the wedging force applied by the jaws 173 of clamp member 172 to press member 178 is to force press member 178 upwards.

During use, a dowel may be:securely held in the jaws 173 of vise module 160 by applying a downward force on the top of press member 178 with a hand. One advantage of this configuration is that a dowel may be more quickly inserted in and removed from jaws 173 of vise module 160 by applying and releasing pressure to press member 178 of the vise module 160 than in a vise where the jaws are moved by the turning of a knob as described above. Another advantage of this configuration is that the dowel may be held more securely in a horizontally and vertically centered position in relation to a cutting tool than with other vise configurations. Yet another advantage of this configuration is that it allows a tighter, more stable grip on a bone dowel than other vise configurations. Still yet another advantage of this configuration is that the vise is infinitely adjustable between the physical limits of travel of the vise jaws, and thus able to hold a bone dowel of any diameter within the limits of travel.

Figure 21:
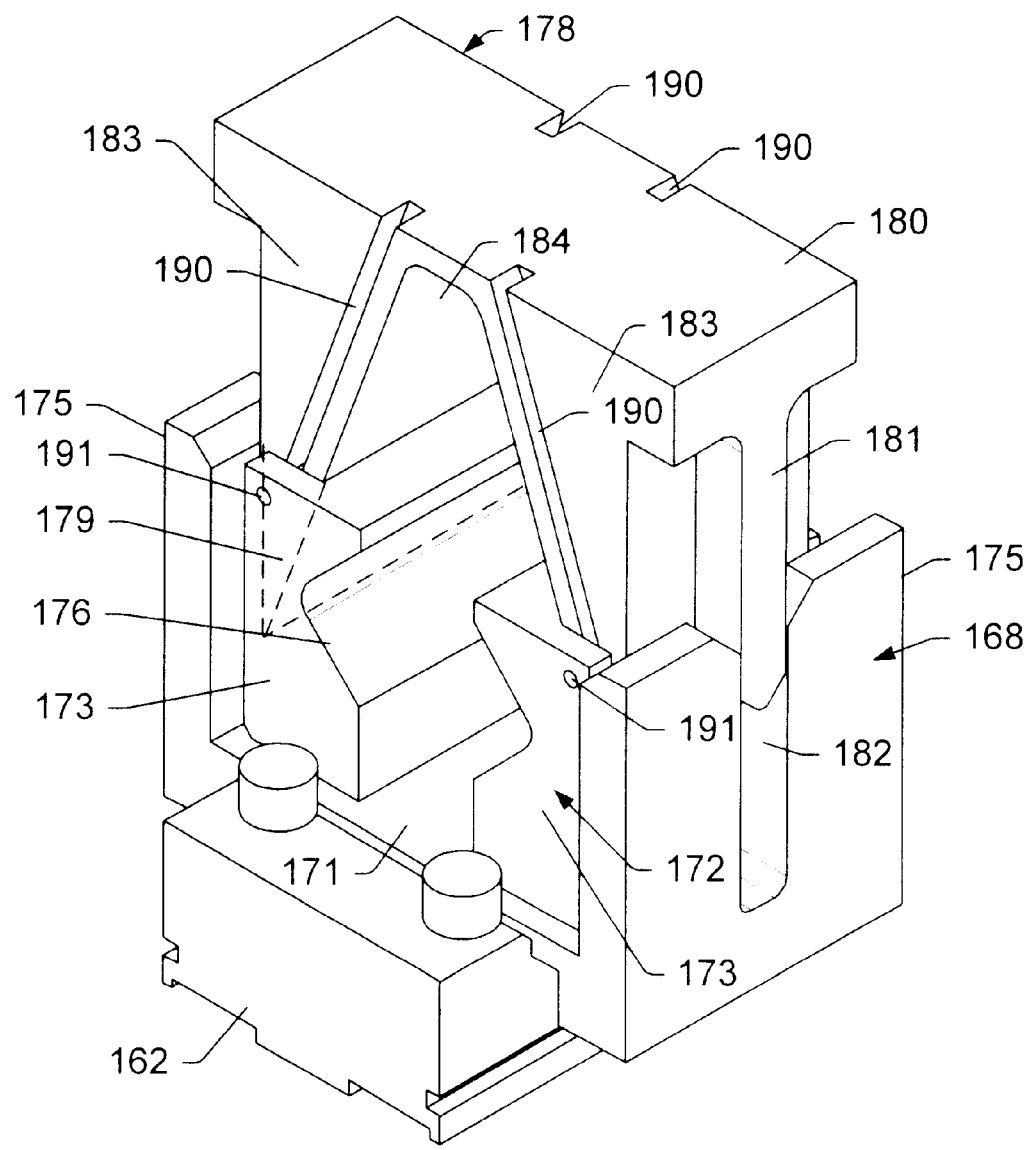
FIG. 21 depicts yet another embodiment of a vise module.

Another embodiment of a vise module 160 is shown in FIG. 21. The vise module 160 may be configured to hold a dowel so that an end of the dowel may be machined. The vise module of FIG. 21 is configured similarly to the vise module of FIG. 19 with the differences noted below. Referring to FIG. 21, the vise module may include a base member 162, a frame member 168, a clamp member 172, and a press member 178. Frame member 168 may include a slot 171 bounded by two sides 175. The two sides 175 of frame member 168 may include slots 182. Press member 178 may include a top 180, a slot 184 enclosed by two arms 183 with angled inside edges, and projections 181 on arms 183. Press member 178 may slidably mate with frame member 168, with the arms 183 of frame member 178 fitting inside the sides 175 of frame member 168, and the projections 181 on the arms 183 fitting inside the slots 182 in the sides 175 of frame member 168. An angled slot 179 may extend substantially down a side of each jaw 173; the slot may be configured to receive an arm 183 of press member 178. The angled slots 179 of the jaws 173 may be angled at a degree complementary to the angled inside edges of the arms 183 of press member 178. Press member 178 may also include grooves 190 extending from the top 180 to the ends of the arms 183, the grooves 190 running substantially parallel to the angled inside edges of the arms 183. The jaws 173 may also include projections on the sides of the angled slots 179 configured to slidably mate with the grooves 190 on the press member 178. In one embodiment (shown here), the projections may be round pins 191 inserted in holes in the sides of the angled slots.

An embodiment of a vise module 160 as shown in FIG. 21 may be assembled by first mounting a frame member 168 on a base member 162 by inserting the frame member in groove 188 and inserting retaining screws 170 into the base member 162. One jaw 173 may then be slidably mounted on each arm 183 of press member 178 by sliding the arm 183 into the angled slot 179 of the jaw 173, with the pins 191 on each side of the angled slot 179 engaging the grooves 190 on the arm 183. The press member 178 with jaws 173 may then be placed in the frame member 168, with the two arms 183 fitting between the angled slots 179 of the jaws 173 and the sides 175 of frame member 168, and the projections 181 on the arms 183 of press member 178 fitting into the slots 182 in the sides 175 of frame member 168. Vise module 160 may be configured so that, in a static state, the weight of press member 178 serves to apply a wedging force to the angled slots 179 of jaws 173, causing the jaws 173 to move toward each other. In one embodiment, the jaws 173 may, in a static state, contact each other. Lifting press member 178 may cause the pins 191 on the jaws 173 to slide in the grooves 190 on the arms 183, effective to move the jaws 173 away from each other.

During use, a dowel may be placed in jaws 173 of vise module 160 by lifting press member 178 and inserting the dowel into the grooves 176 on the jaws 173. The dowel may be securely held in the jaws 173 of vise module 160 by applying a downward force on the top of press member 178 with a hand. One advantage of this configuration is that a dowel may be more quickly inserted in and removed from jaws 173 of vise module 160 by lifting and pressing press member 178 of the vise module 160 than in a vise where the jaws are moved by the turning of a knob as described above. Another advantage of this configuration is that the dowel may be held more securely in a horizontally and vertically centered position in relation to a cutting tool than With other vise configurations.

Figure 22:
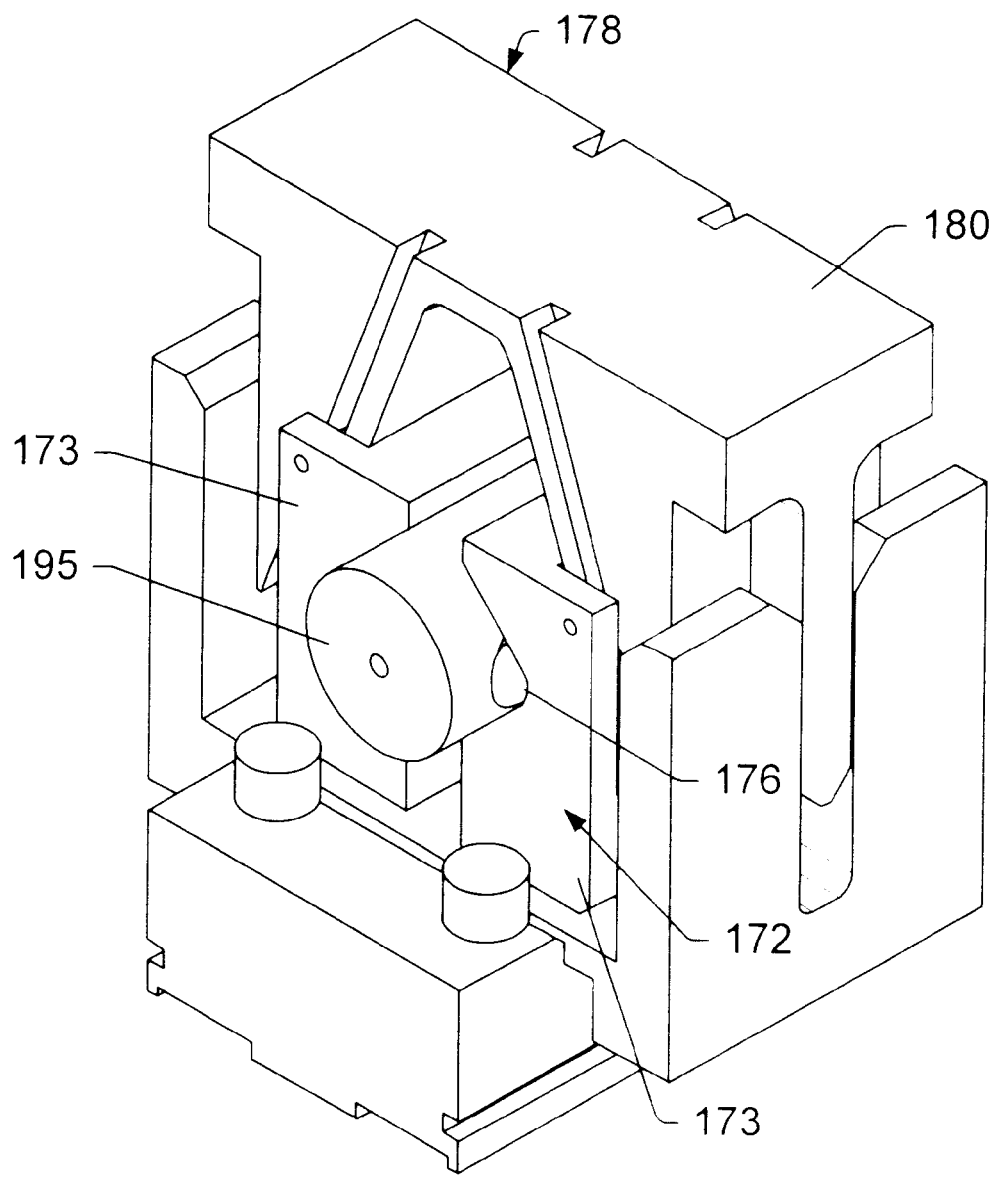
FIG. 22 depicts an embodiment of a vise module holding a bone dowel.

FIG. 22 illustrates a bone dowel 195 held in one embodiment of a vise module 160 as shown in FIG. 21. The grooves 176 in jaws 173 may substantially contact the circumferential outer surface of bone dowel 195. In a static state, the weight of press member 178 may serve to move jaws 173 toward each other with sufficient force to loosely hold bone dowel 195 in grooves 176. Downward force applied to the top 180 of press member 178 may serve to move jaws 173 toward each other with sufficient force to securely hold bone dowel 195 in grooves 176 during the manufacturing process.

During the manufacture of a bone dowel, a vise module is useful for holding a dowel while smoothing an end of the bone dowel and for drilling holes in an end of the dowel. For example, a bone dowel may be held in the vise module with the vise module in the cutting tool track 12 (parallel orientation). FIG. 17 depicts a machine base 11 with a vise module 160 in the parallel orientation as described. In the parallel orientation, vise module 160 may be pushed along a track 12 by a free hand. In some embodiments, a base 162 of vise module 160 may include a stop at one end to limit the distance vise module 160 may be inserted in a track. In one embodiment, retaining screws 170 may extend substantially through base 162 of vise module 160 and may serve as a stop to limit the distance vise module 160 may be inserted in a track. The dowel may be placed in vise module 160 and secured by pressing downward on press member 178 until the pressure of the jaws is sufficient to hold the dowel. The retaining screws 170 may be loosened to allow frame member 168 to slide in the groove 188 of base member 162. During use, the cutting tool motor may be turned on so that the burr is turning at high speed. Initially, frame member 168 may be positioned as far to one side of base member 162 as possible so that the stop 186 is contacting the side of base member 162. By sliding frame member 168 in the groove 188 of base member 162, the dowel may be made to contact the cutting tool burr, thus smoothing the end of the dowel. The dowel may then be repositioned in vise module 160 and the process repeated for the other end of the dowel. Alternatively, vise module 160 may be placed in a track perpendicular to the cutting tool track 12 and the ends of the dowel may be smoothed in a similar method to that described above for collet module 60.

Vise module 160 may be left in the cutting tool track 12 (parallel orientation), frame member 168 may be centered on base member 162, and the retaining screws 170 tightened to secure frame member 168 to base member 162. Vise module 160 holding the dowel may be pushed by hand directly into a turning burr or bit mounted on a cutting tool to drill a hole in an end of the dowel. Alternatively, vise module 160 may be secured in the track 12 and a hole drilled by advancing the cutting tool module towards the dowel by turning the knob 26. The dowel may then be repositioned in vise module 160 and the process repeated for the other end of the dowel. The holes in the ends of the dowels may be useful during the manufacturing process, for example in interacting with a dead center and chuck during the threading process. The holes may also improve bone graffing of the dowel to adjacent vertebrae by providing more space for the packing of osteogenic material, and by providing paths for tissue growth.

The retaining screws 170 may then be loosened to allow frame member 168 to slide in the groove 188 of base member 162. A cutting tool burr configured to produce a straight sided groove or slot may then be mounted on the cutting tool and the tool turned on. Vise module 160 may then be moved towards the cutting tool burr so that the burr contacts the dowel. By sliding frame member 168 in the groove 188 of base member 162, the burr is made to cut a groove or slot in the end of the dowel. The cutting tool module may then be moved closer to vise module 160 and the process repeated to deepen the groove or slot as necessary. A groove typically is a straight cut extending from one side of the end of the dowel to the other. A slot typically is an enclosed cut that does not break the outer wall of the end of the slot. The process may be modified to form various shapes of slots. For example, the dowel may be rotated 90° in the vise and a second cut made to to form a cross-shaped slot. Slot shapes may further include, but are not limited to, rectangular, square, oval, star, triangular, and hexagonal. Slots with multi-sided shapes (all listed above except oval) may be rounded at the comers during the manufacturing process. During surgical implantation of a dowel, such a groove or slot is useful to mate with a driver apparatus. The groove or slot may also be useful during the manufacturing process to interact with a chuck. An enclosed slot is stronger at the ends, and therefore less likely to break during manufacture and insertion, than a groove. Rounding of the corners of the slots further increases the strength of the slot. Also, an enclosed slot leaves a continuous ring of bone around the end of the dowel, increasing the load bearing strength of the end of the dowel after insertion when compared to a groove.

Figure 6:
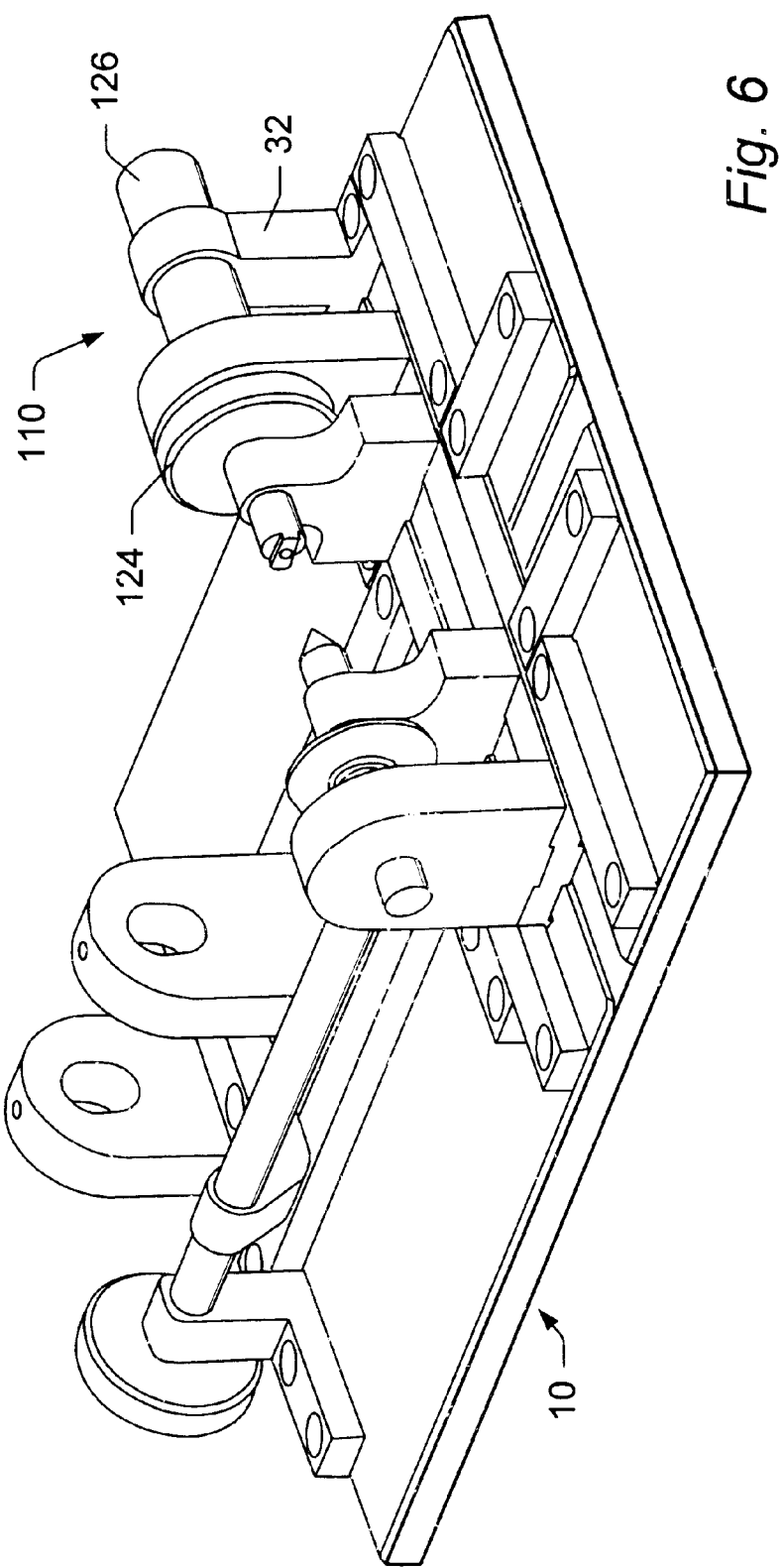
FIG. 6 depicts a machine base with a threading module.
Figure 9:
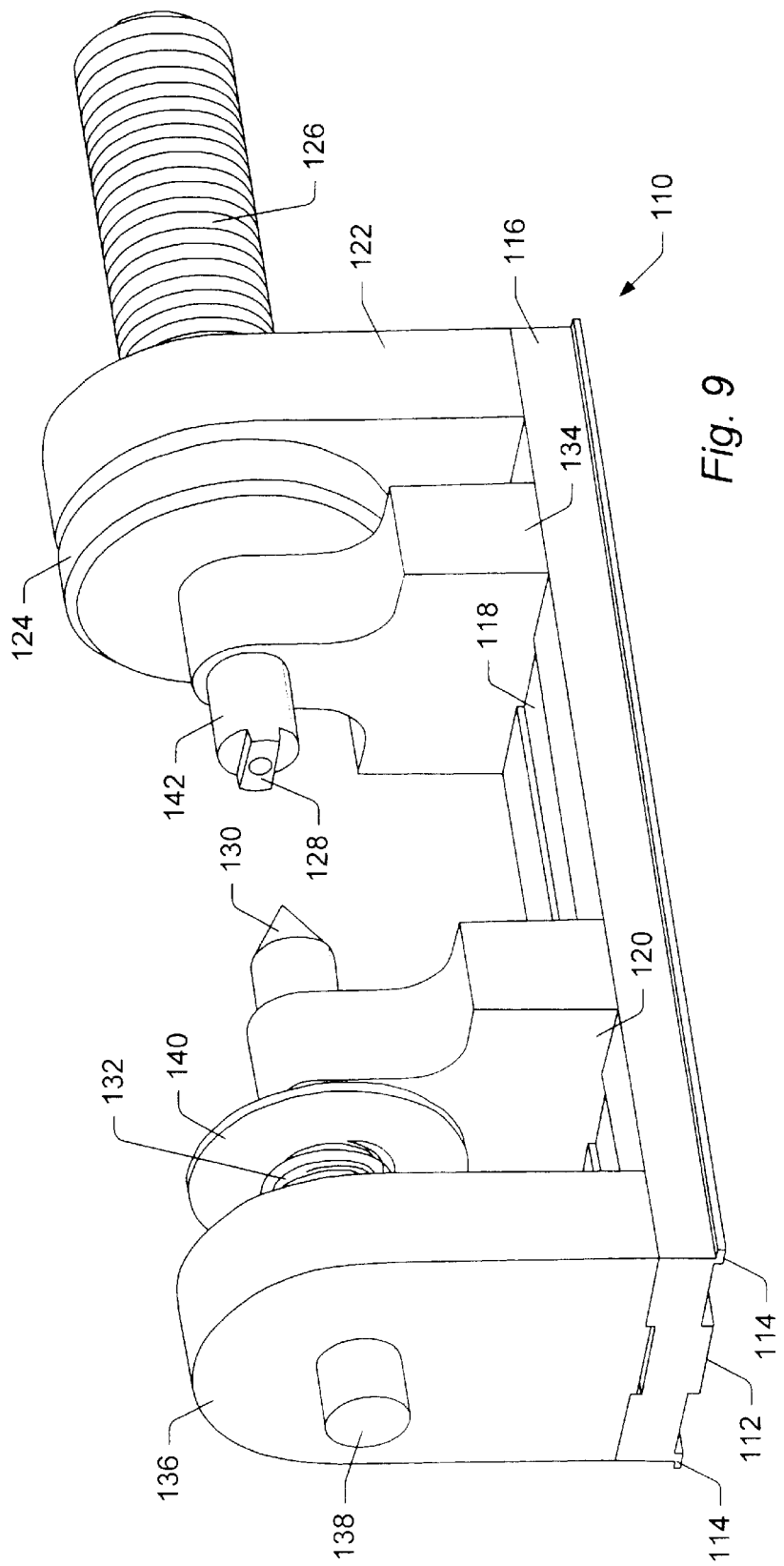
FIG. 9 depicts a threading module.

A machine base 10 with a threading module 110 in the perpendicular orientation is shown in FIG. 6. A threading module 110 is shown in isolation in FIG. 9. The bottom of base 116 of the threading module 110 may have the same configuration as the previously described modules including a projection 112 and flanges 114 for riding in the tracks 12, 14 of machine base 10. Base 116 may also provide a groove 118 for tracking of the moveable member 120 of the threading module 110. The module includes a first support member 136 that provides an opening for a rod 138 that may pass through support member 136 and a moveable member 120, and provide a dead center 130 configured to insert a point into a center hole drilled in the end of a dowel to be threaded. The rod 138 may be bonded to member 120 and may also pass through a spring 132 disposed between member 136 and 120 during use. In the described configuration, the spring biases moveable member 120 toward member 134. A disc 140 may also be coupled to member 120 to provide a solid surface for spring 132.

A threading module 110 may also include an immobile support member 134 that provides a turning member or chuck 142 to hold a dowel to be threaded. As shown, a projection 128 may be provided to mate with a groove or slot machined in an end of the dowel as described herein. The projection 128 is shown as a rectangle, but it is to be understood that the projection may be in the form of a rectangle with rounded corners, an oval, a hexagon, a square, a cross with rounded corners, or any other shape conformed to mate with a groove or slot that may be machined into an end of a dowel. Also included in the embodiment of a threading module 110 is support member 122, which provides an opening for threaded projection 126. Threaded projection 126 may be configured to mate with the threaded opening 32 in support member 30 (FIG. 1). Threaded projection 126 may also be coupled to a knob 124 configured such that turning the knob 124 is effective to thread the projection 126 through the opening 32. The knob 124 may also be coupled to the chuck 142, such that turning the knob 124 also turns a dowel held by the chuck.

Figure 18:
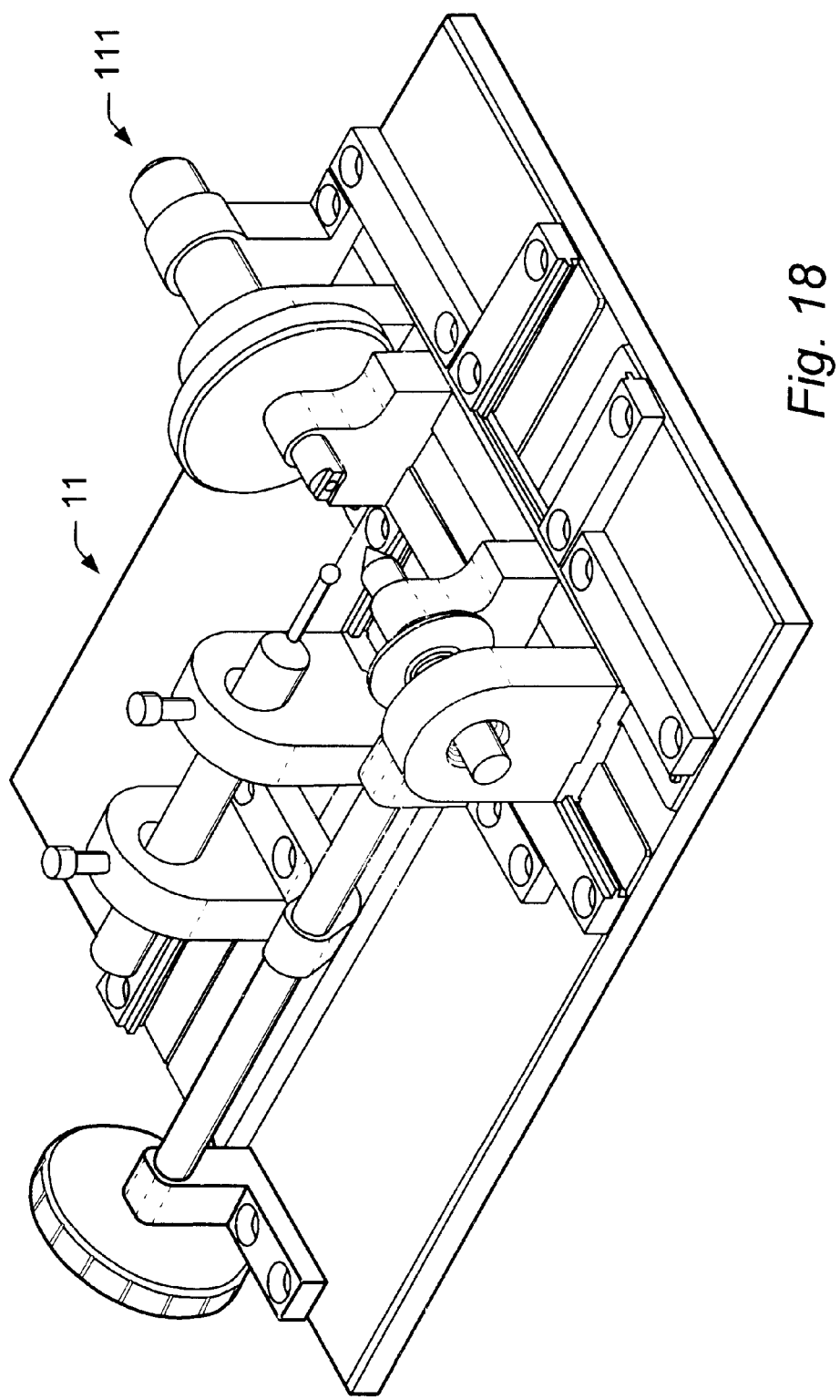
FIG. 18 depicts another embodiment of a machine base with a threading module
Figure 20:
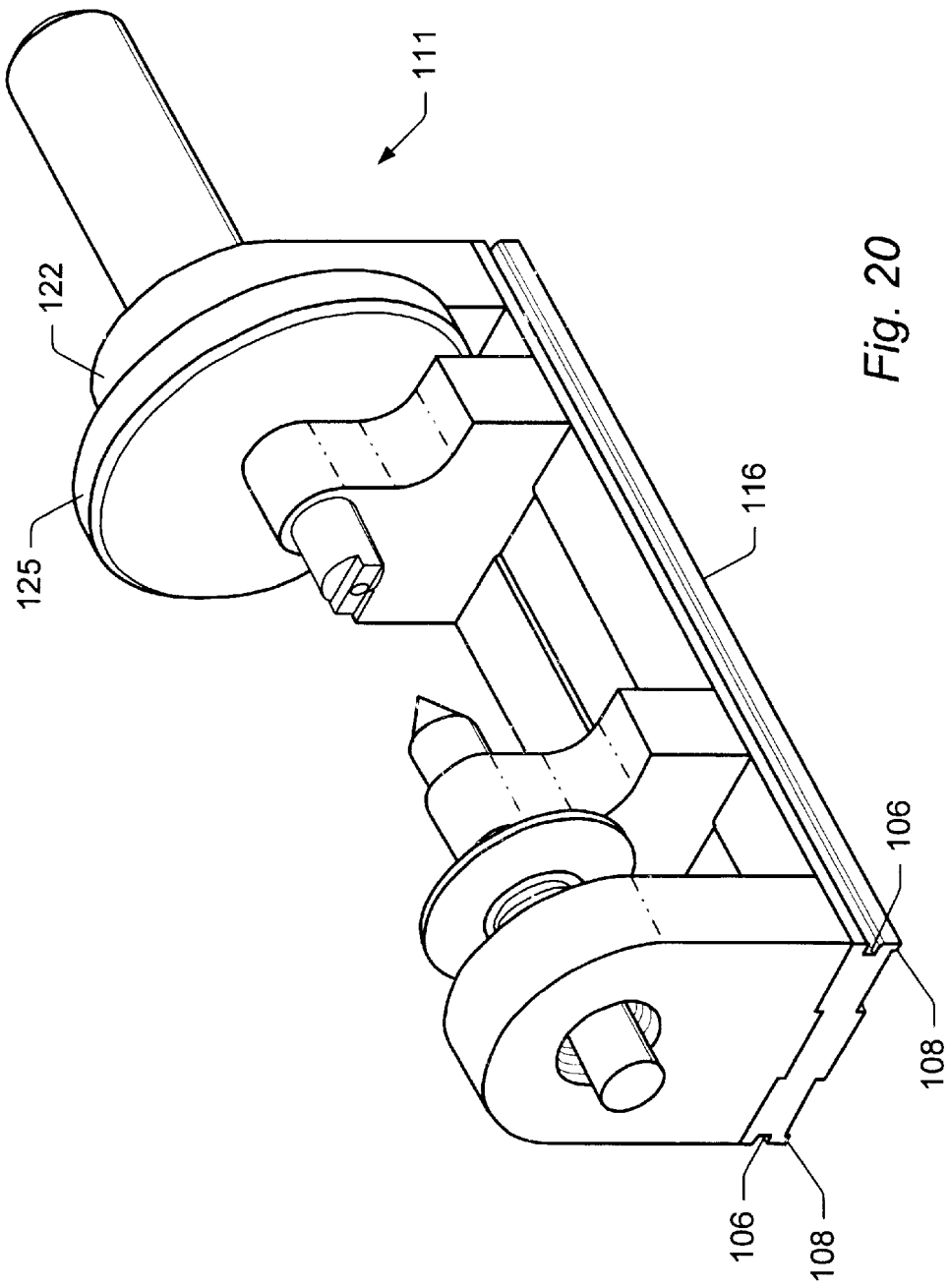
FIG. 20 depicts another embodiment of a threading module.

Another embodiment of a machine base 11 with a threading module 111 in the perpendicular orientation is shown in FIG. 18. A threading module 111 is shown in isolation in FIG. 20. This embodiment may be distinguished by grooves 106 and projections 108 on the base 116 of threading module 111, configured to slidably mate with complementary projections 15 and grooves 17 on the rails 34 of machine base 11. This configuration allows precise, controlled movement of the module through the tracks. Also, the knob 125 may be enlarged to extend past the edge of the support member 122 to facilitate turning of the knob. In some embodiments, the knob 125 may include marks configured so that rotating the knob from one mark to a second mark relative to a fixed position moves the threading module 111 a known distance along a track.

During use, the threading module may be placed on the machine base in the perpendicular orientation with projection 126 threaded through opening 32, and a dowel may be placed in the threading module. The end having a centered drilled hole may contact the dead center, and the grooved or slotted end may contact the other member 142 of the module. The spring may provide the tension to hold a dowel in place. A threading burr may be mounted on the cutting tool and the tool turned on. The cutting tool module may be moved toward the dowel by turning knob 26 as described above until the burr contacts the dowel. The burr may contact the dowel at one end of the dowel. While the burr contacts the dowel, an operator may turn knob 124, threading the projection through opening 32. This motion may serve to move the dowel past the burr and to simultaneously turn the dowel so that a thread is cut in the dowel. The threads in the dowel will thus have the same pitch as the threads in opening 32. The cutting tool may then be moved closer to the dowel and the process repeated to make deeper threads as needed. During the threading process, a threading burr may be used that will produce threads that are rounded at the edges, or the edges may be rounded using a different burr after the threads are cut. Rounding of the threads makes the threads less likely to break at the edges than threads with sharp-angled edges.

Figure 10C:
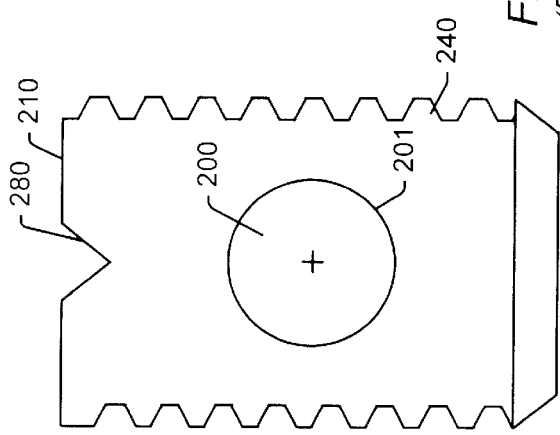
FIG. 10a depicts an example of a bone dowel known in the prior art.
FIG. 10b depicts another example of a bone dowel known in the prior art.
Figure 10D:
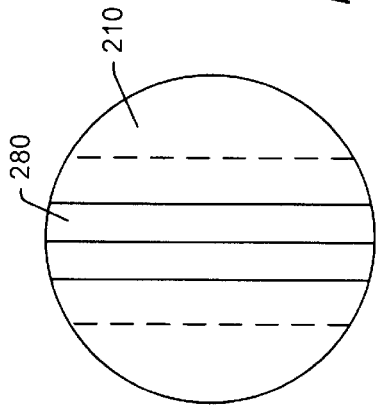
Figure 10A:
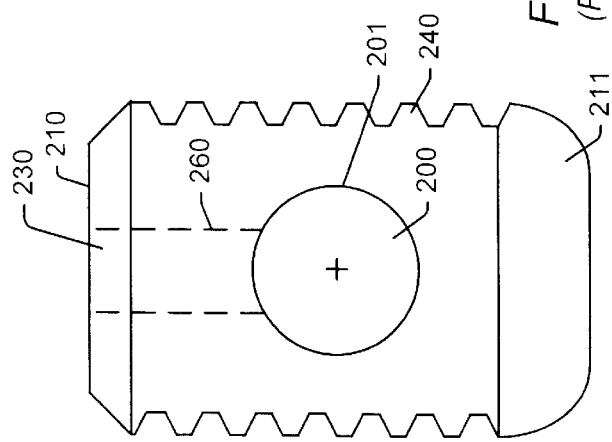
Figure 10B:
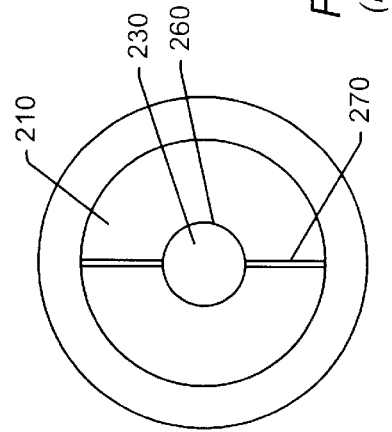

An example of a bone dowel as known in the prior art is depicted in FIG. 10a. The bone dowel includes a canal 200, cancellous bone 201 lining the surface of the canal 200, a first end 210, a second end 211, a hole 230 machined into the first end 210, internal threads 260 in the hole 230, and external threads 240 with angular edges. FIG. 10b is a view of the first end 210 of the bone dowel of FIG. 10a, showing a score mark 270, a hole 230, and internal threads 240.

FIG. 10c shows an example of another bone dowel as known in the prior art. The bone dowel includes a canal 200, cancellous bone 201 lining the surface of the canal 200, a first end 210, a second end 211, a groove 280 extending to the outer edges of the first end 210, and external threads 240 with angular edges. FIG. 10d is a view of the first end 210 of the bone dowel of FIG. 10c, showing the groove 280.

Bone dowels as described above either lack a slot or include an angular-edged groove that extends to the edges of the end of the dowel. Lacking a slot or groove limits the amount of torque that can be applied through an instrument during the surgical insertion of a bone dowel. Grooves that violate the outside edge of the end of the bone dowel weaken the bone at the end. During surgical insertion or removal, applying torque through an instrument to these grooves may result in breakage of the bone at the sharp edges of the grooves, particularly near the outer ends of the groove where it violates the outer edge of the bone dowel. This bone breakage makes it difficult to further insert or remove the bone dowel because applying torque to the instrument may cause the instrument head to slip out of the groove. The presence of angular edges and corners on the grooves increase the likelihood of breakage during insertion. After surgical insertion, the grooved bone dowels have reduced load-bearing ability due to the weakening of the dowels at the end with the groove. It would be desirable for a bone dowel to provide a slot for the application of sufficient torque during insertion. It would also be desirable to limit the likelihood of breakage at the edges of the slot and to minimize the weakening at the end of the bone dowel caused by the slot.

Prior art threaded bone dowels may have angular-edged external threads. The bone near the angular edges tends to be fragile and is prone to breakage during insertion. It would be desirable for a bone dowel to provide a thread configuration that is less prone to breakage.

Some bone dowels of the prior art have canals formed by the intramedullary space of a long bone. In these bone dowels, the marrow may be removed and the space may be packed with osteogenic material prior to surgical insertion. It would be desirable to maximize the amount of space available for the osteogenic material without compromising the strength of the bone dowel.

Some bone dowels of the prior art have holes drilled into one end of the dowel, but lack a hole on the second end. It would be desirable to provide a hole on the second end to aid in the manufacturing process by providing an interface for a module, for example a threading module, with a dead center on one end and a chuck opposed to the dead center.

An embodiment of the bone dowel as produced by the bone dowel manufacturing process described above is shown in FIG. 11. The bone dowel is of a cylindrical shape and includes a canal 300 formed by the intramedullary space of a long bone. The canal surface may be improved by the removal of cancellous bone, promoting better grafting of the bone dowel to adjacent bone structures by increasing the space available for the insertion of osteogenic material without a significant reduction in the strength of the bone dowel. There is also a first end 310, a second end 311, and a slot 320. The slot 320 may be in the shape of a rectangle with rounded corners 321, and may be machined into the first end 310. An advantage of a slot with this configuration is that it does not violate the edge of the end of the bone dowel, which increases the amount of bone material around the slot, and increases the strength of the bone at the end of the slot. Another advantage of the slot configuration is the rounded corners, which are stronger than angular corners. These advantages combine to allow sufficient torque to be applied to the bone dowel during insertion while minimizing the risk of breakage of the bone at the edges of the slot. Also shown in FIG. 11, a bone dowel may include a first hole 330 machined into the first end 310 with optional internal threads 360, and a second hole 331 machined into the second end 311 with optional internal threads 361. The presence of a hole in both ends of the bone dowel aid in the manufacturing process by providing an interface for tools such as dead centers and guides. The holes also provide more space for the insertion of osteogenic material, thus promoting better grafting of the bone dowel to adjacent bone structures. External sinusoidal threads 340 extend the length of the bone dowel. The absence of sharp edges on the threads make them stronger and thus less likely to break during manufacture or during the surgical insertion process. Also appearing are facets 350 that may be the results of the natural geometry of a long bone.

Figure 11:
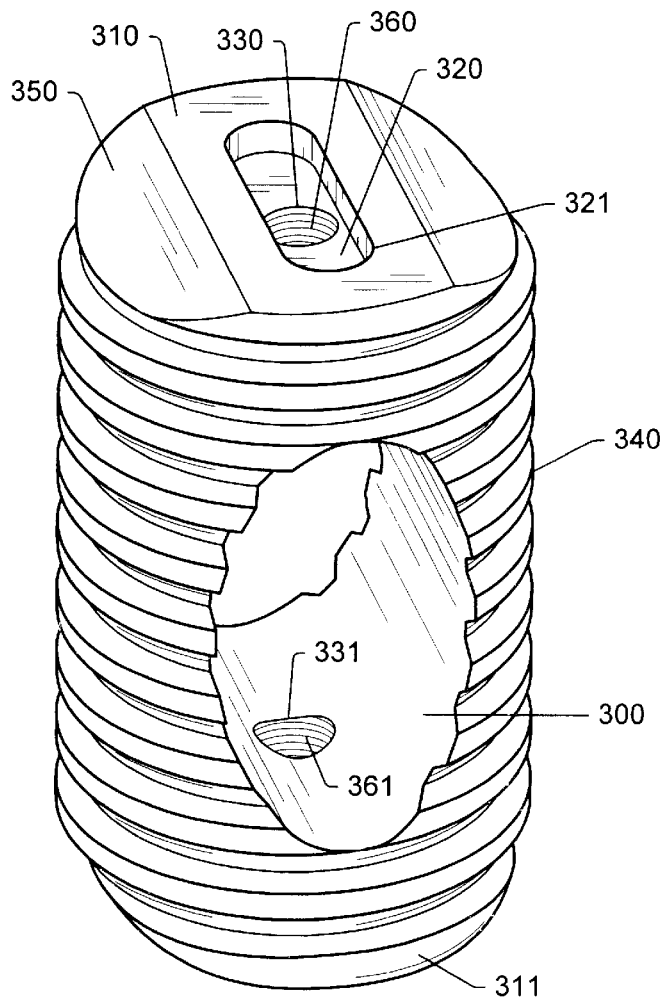
FIG. 11 depicts one embodiment of a bone dowel of this invention.
Figure 12A:
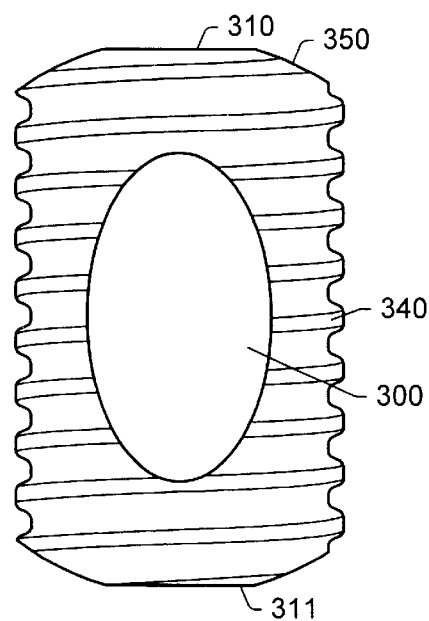
FIG. 12a depicts a front view of the bone dowel of FIG. 10.
Figure 12B:
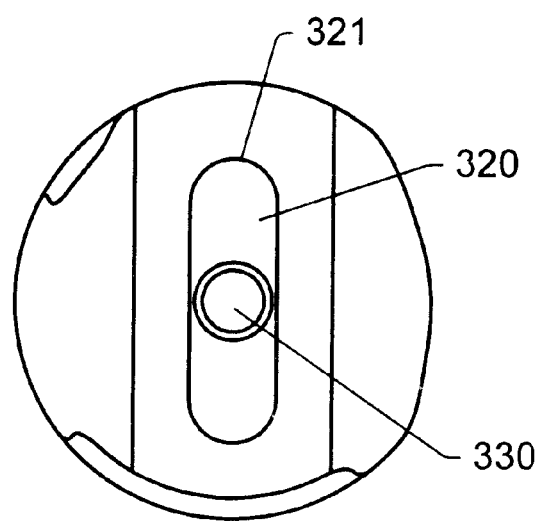
FIG. 12b depicts the first end of the bone dowel of FIG. 10.
Figure 12C:
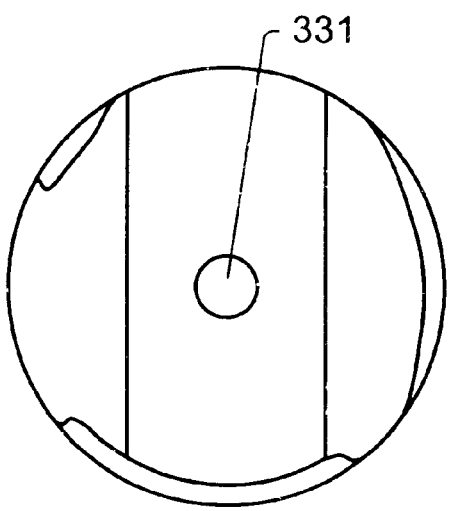
FIG. 12c depicts the second end of the bone dowel of FIG. 10.

FIG. 12a is included to show some of the features of the bone dowel of FIG. 11. In one embodiment, the bone dowel includes a canal 300, a first end 310, a second end 311, sinusoidal threads 340, and optional facets 350. The cancellous bone has been removed from the canal, providing more space for the packing of ostogenic materials. The sinusoidal threads have no angular edges, and are thus resistant to breaking during insertion. FIG. 12b is an overhead view of the first end 310 of the bone dowel of FIG. 11 The first end 310 includes a slot 320 with rounded corners 321. The completely enclosed ends of the slot and the rounded corners reduce the incidence of breakage during insertion. The centered opening of the first hole 330 may be enclosed within the slot 320. FIG. 12c is an overhead view of the second end 311 of the bone dowel of FIG. 11. This view shows the centered opening of the second hole 331 which is useful during the manufacturing process.

FIG. 13a, 13b, 13c, 13d, and 13e show overhead views of the first end 310 of several embodiments of a bone dowel to illustrate several examples of configurations of the slot machined into the end of the bone dowel for the purpose of interacting with a chuck or insertion instrument. FIG. 13a depicts a cross-shaped slot 380 with optionally rounded corners enclosing the centered opening of the first hole 330. FIG. 13b depicts a hexagonal slot 381 whose corners may be optionally rounded enclosing the centered opening of the first hole 330. FIG. 13c depicts an oval-shaped slot 382 enclosing the centered opening of the first hole 330. FIG. 13d depicts a centered opening of the first hole 330 with one circular slot 383 offset from the first hole. FIG. 13e depicts two circular slots 384 and 385 on opposite sides of the centered opening of the first hole 330.

FIG. 14a and 14b show alternative configurations of threads that may be included in some embodiments of a bone dowel. In FIG. 14a, the threads have rectangular bodies 341, radiused top edges 342, radiused bottom corners 343, and flat top, side, and bottom surfaces. FIG. 14b depicts threads with trapezoidal bodies 341, radiused top edges 342, angular bottom corners 343, and flat bottom surfaces 344.

Example of a Bone Dowel Manufacturing Procedure

The first step in a manufacturing procedure may be to determine the size of the first dowel. Donor bone may be first processed according to normal procedures of a bone tissue bank. The largest width of the intramedullary space may be measured and 6 mm may be added to this measurement to determine the smallest possible dowel that can be manufactured. The number may then be rounded up to the closest even number size (14, 16, 18, or 20 mm, for example). Using an oversized hole saw, (14.5, 16.5, 18.5, and 20.5 mm for this example), a cylindrical dowel may be cut from the ring, using care to ensure that the intramedullary space is centered in the dowel. The hole saw may leave a mark or may drill a small hole at the center. The intramedullary space may be then deburred with a small file, and the dowel may be washed and stored.

The next step in processing the bone may be to determine the size of the remaining dowels. The largest width of the exposed intramedullary space may be measured and a ring may be cut with a width equal to this largest width plus 8 mm. The largest width of the exposed intramedullary space may be measured on both sides of the ring and 6 mm may be added to this number to determine the smallest possible dowel that can be manufactured from this ring. The number may be rounded up as above (14, 16, 18, or 20 mm, for example). If the number is smaller than 14 mm, then preferably no dowel is made from that ring. Using an oversized hole saw, a cylindrical dowel may be cut from the ring (14.5, 16.5, 18.5, and 20.5 mm for this example), using care to ensure that the intramedullary space is centered in the dowel. The hole saw may leave a mark or may drill a small hole at the center. A centered hole may be drilled through the length of the dowel while the dowel is still in the hole saw bit by inserting a drill through a guide hole on the end of the hole saw bit. The intramedullary space may be then deburred with a small file, and the dowel may be washed and stored.

The dowels are then machined to length. First the length of the intramedullary space may be measured, 6 mm may be added to the measurement, and the number may be rounded up to determine the smallest possible dowel length (18, 22, or 26 mm, for example). The dowel may be cut with a band saw to 2 mm longer than the length determined as the smallest possible length for that dowel while centering the intramedullary space. The dowel may be then washed and stored.

The dowel prepared as described may be then ready for machining to its final shape. In one embodiment, the machine base may be set up with the cutting tool in place and the burr installed. The dowel may be secured in the collet module, which may be placed in the base oriented perpendicular to the cutting tool. The distal end of the dowel may then be machined until smooth, removing no more than 1 mm. The collet may be then oriented parallel to the cutting tool and a pilot hole may be drilled in the center of the distal end of the dowel, using a drill bit. The dowel may be repositioned in the collet module and the proximal end machined until smooth and a pilot hole drilled as was done to the distal end. In one embodiment, the drilled pilot hole penetrates to the intramedullary space. A burr may then be placed on the cutting tool and the dowel may be placed in the vise module. The vise module may be placed in the machine base in the parallel orientation and a groove or slot machined into the proximal end of the dowel.

The procedure listed above may be performed differently in other embodiments of a bone dowel machine. The machine base may be set up with the cutting tool in place and the burr installed. The dowel may be secured in a vise module, which may be placed in the base oriented parallel to the cutting tool. The sliding portion of the vise may then be loosened and the distal end of the dowel may be machined until smooth, removing no more than 1 mm. The sliding portion of the vise may then be centered and secured and a pilot hole may be drilled in the center of the distal end of the dowel, using a drill bit. The dowel may be repositioned in the vise module and the proximal end machined until smooth and a pilot hole drilled as was done to the distal end. In one embodiment, the drilled pilot hole penetrates to the intramedullary space. In some embodiments, a thread tap may be used to form threads along a portion of the length of one or both of the pilot holes. In other embodiments, the ends of the dowel may not be smoothed as described above. A burr may then be placed on the cutting tool, the sliding portion of the vise loosened, and a groove or slot may be machined into the proximal end of the dowel.

In some manufacturing procedures, an alternative method may be used to drill a centered hole lengthwise in the bone dowel. After cutting a bone dowel from a donor bone with a hole saw, the hole saw bit may be used as a center hole drill guide. The hole saw bit may be removed from the saw motor and the bone dowel may be left in the hole saw bit. A drill may be used to drill a centered hole lengthwise through the bone dowel by drilling through a guide hole in an end of the hole saw bit. The bone dowel may then be removed from the hole saw bit.

The dowel may be next mounted in the threading module, which may be placed in the machine base in the perpendicular orientation. The dowel may be preferably mounted by supporting the pilot hole in the distal end of the dowel with the dead center and capturing the proximal end by the hole and groove or slot. The thread cutting burr may be mounted on the cutting tool. Before cutting, the threading module may be moved into the base as far as possible. The cutting tool may be turned on and advanced until the burr touches the dowel. The knob on the threading module may then be turned until the entire dowel has moved past the burr. The threading module may then be returned to the starting position, the burr may be advanced approximately 0.020 inches, and the knob may be turned to move the dowel past the burr. The diameter of the dowel may then be measured using calipers, for example, and the process repeated until the desired diameter is achieved. The dowel may then be processed, packaged and stored according to normal tissue bank procedures, or it may be used in surgery immediately.

While the devices and methods of this disclosure have been described in terms of preferred embodiments, it will be apparent to those of skill in the art that variations may be applied to the devices, methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A device for manufacturing a bone dowel comprising:
   a machine base comprising at least one track;
   a module for holding a rotary cutting tool, wherein the module comprises a base configured to slide in the track;
   a vise module comprising a base configured to slide in the track and a vise configured to hold a bone portion during use; and
   a threading module comprising a base configured to slide in the track, a dead center, and a chuck opposed to the dead center, wherein the threading module is configured to hold a bone portion during use;
   wherein the device is adapted to make a bone dowel during use.

2. The device of claim 1, wherein the machine base comprises two or more tracks, and wherein at least one track is perpendicular to at least one other track.

3. The device of claim 1, wherein the vise module is configured to hold the bone portion along the length thereof such that an end of the bone portion may contact a cutting tool during use.

4. The device of claim 1, wherein the threading module is configured such that a circumferential portion of the bone portion rotating in the threading module may contact a cutting tool during use.

5. The device of claim 1, further comprising a high speed rotary cutting tool configured to cut a bone portion during use.

6. The device of claim 1, further comprising a support member coupled to the track, the support member comprising a threaded opening.

7. The device of claim 1, wherein the machine base comprises a support member comprising a threaded opening coupled to the track, and wherein the threading module comprises a threaded projection configured to threadably mate with the threaded opening such that turning the threaded projection is effective to move the threading module in the track, and to turn a bone portion held in the threading module.

8. The device of claim 1, wherein the module for holding a rotary cutting tool is disposed in the track and comprises an arm rigidly coupled to the module and configured to threadably engage a threaded rod, wherein rotation of the rod is effective to move the module in the track.

9. The device of claim 8, further comprising a knob coupled to the rod, wherein the knob comprises a plurality of marks configured such that turning the knob from a first mark to a second mark relative to a fixed position moves the module a known distance in the track during use.

10. The device of claim 1, wherein each track comprises a plurality of marks disposed along the length thereof for measuring the movement of modules mounted in the tracks during use.

11. The device of claim 1, wherein the device is autoclavable.

12. The device of claim 1, wherein each track comprises two rails that extend the length of the track and define the outer boundaries of the track, and wherein each rail comprises at least one projection and one groove, and wherein each module base comprises at least one projection and one groove, and wherein the grooves on each of the module bases are configured to slidably mate with the projection on the rail, and wherein the projections on each of the module bases are configured to slidably mate with the groove of the rail.

13. The device of claim 1, wherein each track comprises a groove extending the length of the track, and wherein each module base comprises a projection, and wherein the projection is configured to slidably mate with the groove of the track.

14. The device of claim 1, wherein the vise comprises:
    a frame comprising a bottom and two opposing walls extending upwards from the bottom;
    a pair of opposing mobile vise jaws coupled to the bottom of the frame and adapted to hold a bone portion during use; and
    a press configured to rest on the vise jaws;
    wherein applying a force to the press is effective to vary a distance between the vise jaws.

15. The device of claim 14, wherein the vise jaws are slidably disposed on the bottom of the frame.

16. The device of claim 14, wherein the press comprises a top and two opposing arms extending downwards from the top, wherein outer surfaces of the arms of the press slidably mate with inner surfaces of the walls of the frame, and outer surfaces of the vise jaws slidably mate with inner surfaces of the arms of the press.

17. The device of claim 14, wherein the press is effective to move the vise jaws together when the press is moved toward the bottom of the frame during use.

18. The device of claim 14, wherein the press is effective to move the vise jaws apart when the press is moved away from the bottom of the frame during use.

19. The device of claim 14, further comprising a spring device coupled to the vise jaws, wherein the spring device is configured to apply a force on each of the vice jaws such that the vise jaws are moved away from each other during use.

20. The device of claim 19, wherein the movement of the vise jaws away from each other is effective to push the press away from the bottom of the frame.

21. The device of claim 19, wherein an inner surface of each of the vice jaws comprises at least one hole drilled partially through the vice jaw, and wherein the hole is configured to accept one end of the spring device, and wherein the hole secures the spring device in place during use.

22. The device of claim 14, wherein the vise module base comprises a top, a bottom, two ends, and two sides, and wherein the frame is configured to slide on the vise module base.

23. The device of claim 22, wherein the bottom of the vise module base comprises a stop, and wherein the stop is configured to limit the distance the vise module is inserted in a track during use.

24. The device of claim 24, wherein the top of the vise module base comprises a groove extending from one side of the base to the other side of the base, the groove configured to slidably mate with the bottom of the frame.

25. The device of claim 24, wherein the vise module base further comprises at least one fastening device disposed on each side of the groove, wherein tightening of the fastening devices prevents the frame from sliding in the groove, and wherein loosening of the fastening devices releases the frame to slide in the groove.

26. The device of claim 25, wherein the vise module base further comprises at least one threaded hole disposed on each side of the groove, and wherein the fastening devices are screws, and wherein the screws are configured to be threaded into the threaded holes on each side of the groove.

27. The device of claim 26, wherein the threaded holes on one side of the groove extend through the vise module base from the top to the bottom, and wherein the length of the screws threaded in the holes is substantially longer than the holes, such that the ends of the screws extend substantially past the bottom of the vise module base, and wherein the ends of the screws extending past the bottom of the vise module base are effective to limit the distance the vise module is inserted in a track during use.

28. The device of claim 24, wherein the bottom of the frame further comprises stops extending downward at each end of the bottom, and wherein the stops serve to limit the sliding motion of the frame within the groove on the vise module base.

29. The device of claim 16, wherein each wall of the frame further comprises at least one slot extending downward from the top of the wall towards the bottom of the frame.

30. The device of claim 29, wherein each arm of the press further comprises at least one projection on an outside surface of the arm, and wherein the projection is configured to slidably mate with the slot on the wall of the frame adjacent to the arm during use.

31. The device of claim 16, wherein inner surfaces of the arms of the press are sloped such that the inner surfaces of the arms diverge as they extend from the top of the press to ends of the arms.

32. The device of claim 16, wherein each vise jaw further comprises a groove on an outer surface, and wherein the arms of the press slidably fit in the grooves on the outer surfaces of the vice jaws.

33. The device of claim 32, wherein the groove on the outer surface of the vice jaw extends from the top of the vise jaw downwards a substantial distance towards the bottom of the vise jaw, and wherein the bottom of the groove is sloped so that it is deepest at the top of the vise jaw, and wherein the slope of the inner surfaces of the arms is complementary to the slope of the bottom of the grooves, so that the contact of the inner surfaces of the arms with the bottoms of the grooves is effective to move the vise jaws together when the press is moved towards the bottom of the frame during use.

34. The device of claim 32, wherein sides of the grooves on the outer surfaces of the vise jaws comprise at least one projection, and wherein sides of the arms of the press comprise at least one groove, and wherein the projections on the sides of the grooves on the outer surfaces of the vice jaws are configured to slidably mate with the grooves on the sides of the arms.

35. The device of claim 34, wherein the sliding action of the projections on the sides of the grooves on the outer surfaces of the vise jaws when mated with the grooves on the sides of the arms is effective to move the vise jaws apart when the press is moved away from the bottom of the frame during use.

36. The device of claim 34, wherein the projections on the sides of the grooves on the outer surfaces of the vise jaws are substantially round pins fixably attached in holes in the sides of the grooves.

37. The device of claim 32, wherein sides of the grooves on the outer surface of the vise jaws comprise at least one groove, and wherein sides of the arms of the press comprise at least one projection, and wherein the grooves on the sides of the grooves on the outer surfaces of the vise jaws are configured to slidably mate with the projections on the sides of the arms.

38. The device of claim 14, wherein an inner surface of each vise jaw further comprises at least one horizontal groove configured to hold a bone portion during use.

39. The device of claim 38, wherein the horizontal groove on the inner surface of each vise jaw comprises a roughened surface configured to increase the frictional grip on the outer surface of the bone portion during use.

40. The device of claim 1, wherein the cutting tool module further comprises at least one cutting tool support disposed on top of the cutting tool base, wherein the cutting tool support comprises:
  an opening configured to hold the cutting tool so that the cutting tool is oriented parallel to the track;
  at least one threaded hole extending from an outer surface of the cutting tool support to the opening;
  a threaded fastening device that threadably mates with the threaded hole; and
  wherein the threaded fastening device is configured to be tightened in the threaded hole until contacting the outer surface of the cutting tool disposed in the opening, and wherein further tightening of the threaded fastening device serves to secure the cutting tool in the support during use.

41. A system for manufacturing a bone dowel comprising:
a center hole drill guide comprising a body, a first end, and a second end, wherein the first end comprises an opening configured to accept a bone portion, and wherein the second end comprises a centered hole configured to accept a drill bit;
a high speed rotary cutting tool configured to cut a bone portion during use;
a machine base comprising at least one track;
a module for holding the rotary cutting tool, wherein the module comprises a base configured to slide in the track;
a vise module comprising a base configured to slide in the track and a vise configured to hold a bone portion; and
a threading module comprising a base configured to slide in the track, a dead center, and a chuck opposed to the dead center, wherein the threading module is configured to hold a bone portion during use.

42. The system of claim 41, wherein the machine base comprises two or more tracks, and wherein at least one track is perpendicular to at least one other track.

43. The system of claim 41, wherein the center hole drill guide is a hole saw bit.

44. The system of claim 41, wherein the vise module is configured to hold the bone portion along the length thereof such that an end of the bone portion may contact a cutting tool during use.

45. The system of claim 41, wherein the threading module is configured such that a circumferential portion of the bone portion rotating in the threading module may contact a cutting tool during use.

46. The system of claim 41, further comprising a support member coupled to the track, the support member comprising a threaded opening.

47. The system of claim 41, wherein the machine base comprises a support member comprising a threaded opening coupled to the track, and wherein the threading module comprises a threaded projection configured to threadably mate with the threaded opening such that turning the threaded projection is effective to move the threading module in the track, and to turn a bone portion held in the threading module.

48. The system of claim 41, wherein the module for holding the rotary cutting tool is disposed in the track and comprises an aim rigidly coupled to the module and configured to threadably engage a threaded rod, wherein rotating the rod is effective to move the module in the track.

49. The system of claim 48, further comprising a knob coupled to the rod, wherein the knob comprises a plurality of marks configured such that turning the knob from a first mark to a second mark relative to a fixed position moves the module a known distance in the track during use.

50. The system of claim 41, wherein each track comprises a plurality of marks disposed along the length thereof for measuring the movement of modules mounted in the tracks during use.

51. The system of claim 41, wherein each track comprises two rails that extend the length of the track and define the outer boundaries of the track, and wherein each rail comprises at least one projection and one groove, and wherein each module base comprises at least one projection and one groove, and wherein the grooves on each of the module bases are configured to slidably mate with the projection on the rail, and wherein the projections on each of the module bases are configured to slidably mate with the groove of the rail.

52. The system of claim 41, wherein each track comprises a groove extending the length of the track, and wherein each module base comprises a projection, and wherein the projection is configured to slidably mate with the groove of the track.

53. The system of claim 41, wherein the vise comprises:
a frame comprising a bottom and two opposing walls extending upwards from the bottom;
a pair of opposing mobile vise jaws coupled to the bottom of the frame and adapted to hold a bone portion during use; and
a press configured to rest on the vise jaws;
wherein applying a force to the press is effective to vary a distance between the vise jaws.

54. The system of claim 53, wherein the vise jaws are slidably disposed on the bottom of the frame.

55. The system of claim 53, wherein the press comprises a top and two opposing arms extending downwards from the top, wherein outer surfaces of the arms of the press slidably mate with inner surfaces of the walls of the frame, and outer surfaces of the vise jaws slidably mate with inner surfaces of the arms of the press.

56. The system of claim 53, wherein the press is effective to move the vise jaws together when the press is moved toward the bottom of the frame during use.

57. The system of claim 53, wherein the press is effective to move the vise jaws apart when the press is moved away from the bottom of the frame during use.

58. The system of claim 53, further comprising a spring device coupled to the vise jaws, wherein the spring device is configured to apply a force on each of the vice jaws such that the vise jaws are moved away from each other during use.

59. The system of claim 58, wherein the movement of the vise jaws away from each other is effective to push the press away from the bottom of the frame.

60. The system of claim 58, wherein an inner surface of each of the vice jaws comprises at least one hole drilled partially through the vice jaw, and wherein the hole is configured to accept one end of the spring device, and wherein the hole secures the spring device in place during use.

61. The system of claim 53, wherein the vise module base comprises a top, a bottom, two ends and two sides, and wherein the frame is configured to slide on the vise module base.

62. The system of claim 61, wherein the bottom of the vise module base comprises a stop, and wherein the stop is configured to limit the distance the vise module is inserted in a track during use.

63. The system of claim 61, wherein the vise module base further comprises a groove running from one side of the base to the other side of the base, the groove configured to slidably mate with the bottom of the frame.

64. The system of claim 63, wherein the vise module base further comprises at least one fastening device disposed on each side of the groove, wherein tightening of the fastening devices prevents the frame from sliding in the groove, and wherein loosening of the fastening devices releases the frame to slide in the groove.

65. The system of claim 64, wherein the vise module base further comprises at least one threaded hole disposed on each side of the groove, and wherein the fastening devices are screws, and wherein the screws are configured to be threaded into the threaded holes on each side of the groove.

66. The system of claim 65, wherein the threaded holes on one side of the groove extend through the vise module base from the top to the bottom, and wherein the length of the screws threaded in the holes is substantially longer than the holes, such that the ends of the screws extend substantially past the bottom of the vise module base, and wherein the ends of the screws extending past the bottom of the vise module base are effective to limit the distance the vise module is inserted in a track during use.

67. The system of claim 63, wherein the bottom of the frame further comprises stops extending downward at each end of the bottom, and wherein the stops serve to limit the sliding motion of the frame within the groove on the vise module base.

68. The system of claim 55, wherein each wall of the frame further comprises at least one slot extending downward from the top of the wall towards the bottom of the frame.

69. The system of claim 68, wherein each arm of the press further comprises at least one projection on an outside surface of the arm, and wherein the projection is configured to slidably mate with the slot on the wall of the frame adjacent to the arm during use.

70. The system of claim 55, wherein inner surfaces of the arms of the press are sloped such that the inner surfaces of the arms diverge as they extend from the top of the press to ends of the arms.

71. The system of claim 55, wherein each vise jaw further comprises a groove on an outer surface, and wherein the arms of the press slidably fit in the grooves on the outer surfaces of the vice jaws.

72. The system of claim 71, wherein the groove on the outer surface of the vice jaw extends from the top of the vise jaw downwards a substantial distance towards the bottom of the vise jaw, and wherein the bottom of the groove is sloped so that it is deepest at the top of the vise jaw and wherein the a slope of the inner surfaces of the arms is complementary to the slope of the bottom of the grooves, so that the contact of the inner surfaces of the arms with the bottoms of the grooves is effective to move the vise jaws together when the press is moved towards the bottom of the frame during use.

73. The system of claim 71, wherein sides of the grooves on the outer surfaces of the vise jaws comprise at least one projection, and wherein sides of the arms of the press comprise at least one groove, and wherein the projections on the sides of the grooves on the outer surfaces of the vice jaws are configured to slidably mate with the grooves on the sides of the arms.

74. The system of claim 73, wherein the sliding action of the projections on the sides of the grooves on the outer surfaces of the vise jaws when mated with the grooves on the sides of the arms is effective to move the vise jaws apart when the press is moved away from the bottom of the frame during use.

75. The system of claim 73, wherein the projections on the sides of the grooves on the outer surfaces of the vise jaws are substantially round pins fixably attached in holes in the sides of the grooves.

76. The system of claim 71, wherein sides of the grooves on the outer surface of the vise jaws comprise at least one groove, and wherein sides of the arms of the press comprise at least one projection, and wherein the grooves on the sides of the grooves on the outer; surfaces of the vise jaws are configured to slidably mate with the projections on the sides of the arms.

77. The system of claim 53, wherein an inner surface of each vise jaw further comprises at least one horizontal groove configured to hold a bone portion during use.

78. The system of claim 77, wherein the horizontal groove on the inner surface of each vise jaw comprises a roughened surface configured to increase the frictional grip on the outer surface of the bone portion during use.

79. The system of claim 41, wherein the cutting tool module further comprises at least one cutting tool support disposed on top of the cutting tool base, wherein the cutting tool support comprises:

an opening configured to hold the cutting tool so that the cutting tool is oriented parallel to the track;

at least one threaded hole extending from an outer surface of the cutting tool support to the opening;

a threaded fastening device that threadably mates with the threaded hole; and wherein the threaded fastening device is configured to be tightened in the threaded hole until contacting the outer surface of the cutting tool disposed in the opening, and wherein further tightening of the threaded fastening device serves to secure the cutting tool in the support during use.

\* \* \* \* \*

UNITED STATES PATENT AND TRADEMARK OFFICE
CERTIFICATE OF CORRECTION

PATENT NO. : 6,557,226 B1  Page 1 of 1
DATED : May 6, 2003
INVENTOR(S) : Landry et al.

It is certified that error appears in the above-identified patent and that said Letters Patent is hereby corrected as shown below:

Column 25,
Line 32, please delete "vise jaw and" and substitute therefor -- vise jaw, and --.
Line 33, please delete "a slope of" and substitute therefor -- slope of --.

Column 26,
Line 16, please delete "outer; surfaces" and substitute therefor -- outer surfaces --.

Signed and Sealed this

Twenty-ninth Day of July, 2003

JAMES E. ROGAN
*Director of the United States Patent and Trademark Office*